United States Patent
Wang et al.

(10) Patent No.: US 9,956,690 B2
(45) Date of Patent: May 1, 2018

(54) PROTOCOL FOR A REMOTELY CONTROLLED VIDEOCONFERENCING ROBOT

(71) Applicant: INTOUCH TECHNOLOGIES, INC., Goleta, CA (US)

(72) Inventors: Yulun Wang, Goleta, CA (US); Charles S. Jordan, Santa Barbara, CA (US); Marco Pinter, Santa Barbara, CA (US); Jonathan Southard, Santa Barbara, CA (US)

(73) Assignee: INTOUCH TECHNOLOGIES, INC., Goleta, CA (US)

( * ) Notice: Subject to any disclaimer, the term of this patent is extended or adjusted under 35 U.S.C. 154(b) by 0 days. days.

(21) Appl. No.: 15/195,410

(22) Filed: Jun. 28, 2016

(65) Prior Publication Data

US 2016/0303740 A1    Oct. 20, 2016

Related U.S. Application Data

(60) Continuation of application No. 12/819,127, filed on Jun. 18, 2010, now Pat. No. 9,375,843, which is a
(Continued)

(51) Int. Cl.
*B25J 9/00* (2006.01)
*B25J 9/16* (2006.01)
(Continued)

(52) U.S. Cl.
CPC .......... *B25J 9/1697* (2013.01); *G05D 1/0038* (2013.01); *G05D 1/0246* (2013.01);
(Continued)

(58) Field of Classification Search
USPC .......................... 700/245–264; 318/567–569
See application file for complete search history.

(56) References Cited

U.S. PATENT DOCUMENTS

| | | | |
|---|---|---|---|
| 3,821,995 A | 7/1974 | Aghnides | |
| 4,107,689 A * | 8/1978 | Jellinek .................. | G01C 21/12 340/991 |

(Continued)

FOREIGN PATENT DOCUMENTS

| | | |
|---|---|---|
| AU | 1216200 A | 5/2000 |
| CA | 2289697 A1 | 11/1998 |

(Continued)

OTHER PUBLICATIONS

Screenshot Showing Google Date for Lemaire Telehealth Manual, screenshot retrieved on Dec. 18, 2014, 1 page.
(Continued)

*Primary Examiner* — Jonathan L Sample

(57) ABSTRACT

A robotic system that includes a robot and a remote station. The remote station can generate control commands that are transmitted to the robot through a broadband network. The control commands can be interpreted by the robot to induce action such as robot movement or focusing a robot camera. The robot can generate reporting commands that are transmitted to the remote station through the broadband network. The reporting commands can provide positional feedback or system reports on the robot.

2 Claims, 9 Drawing Sheets

Related U.S. Application Data division of application No. 10/732,056, filed on Dec. 9, 2003, now Pat. No. 7,813,836.

(51) Int. Cl.
  *G05D 1/00* (2006.01)
  *G05D 1/02* (2006.01)
  *G06F 19/00* (2018.01)

(52) U.S. Cl.
  CPC ....... *G05D 1/0272* (2013.01); *G06F 19/3418* (2013.01); *G05D 2201/0206* (2013.01); *G05D 2201/0211* (2013.01); *Y10S 901/47* (2013.01)

(56) References Cited

U.S. PATENT DOCUMENTS

| | | |
|---|---|---|
| 4,213,182 A | 7/1980 | Eichelberger et al. |
| 4,413,693 A | 11/1983 | Derby |
| 4,471,354 A | 9/1984 | Smith |
| 4,519,466 A | 5/1985 | Shiraishi |
| 4,553,309 A | 11/1985 | Hess et al. |
| 4,572,594 A | 2/1986 | Schwartz |
| 4,625,274 A | 11/1986 | Schroeder |
| 4,638,445 A | 1/1987 | Mattaboni |
| 4,652,204 A | 3/1987 | Arnett |
| 4,669,168 A | 6/1987 | Tamura et al. |
| 4,679,152 A | 7/1987 | Perdue |
| 4,697,278 A * | 9/1987 | Fleischer ............... G01C 22/02 235/95 B |
| 4,697,472 A | 10/1987 | Hiyane |
| 4,709,265 A | 11/1987 | Silverman et al. |
| 4,733,737 A | 3/1988 | Falamak |
| 4,751,658 A | 6/1988 | Kadonoff et al. |
| 4,766,581 A | 8/1988 | Korn et al. |
| 4,777,416 A | 10/1988 | George et al. |
| 4,797,557 A | 1/1989 | Ohman |
| 4,803,625 A | 2/1989 | Fu et al. |
| 4,847,764 A | 7/1989 | Halvorson |
| 4,875,172 A | 10/1989 | Kanayama |
| 4,878,501 A | 11/1989 | Shue |
| 4,942,512 A | 7/1990 | Kohno |
| 4,942,538 A | 7/1990 | Yuan et al. |
| 4,953,159 A | 8/1990 | Hayden et al. |
| 4,974,607 A | 12/1990 | Miwa |
| 4,977,971 A | 12/1990 | Crane et al. |
| 5,006,988 A | 4/1991 | Borenstein et al. |
| 5,040,116 A | 8/1991 | Evans et al. |
| 5,051,906 A | 9/1991 | Evans et al. |
| 5,073,749 A | 12/1991 | Kanayama |
| 5,084,828 A | 1/1992 | Kaufman et al. |
| 5,130,794 A | 7/1992 | Ritchey |
| 5,148,591 A | 9/1992 | Pryor |
| 5,153,833 A | 10/1992 | Gordon et al. |
| 5,155,684 A | 10/1992 | Burke et al. |
| 5,157,491 A | 10/1992 | Kassatly |
| 5,182,641 A | 1/1993 | Diner et al. |
| 5,186,270 A | 2/1993 | West |
| 5,193,143 A | 3/1993 | Kaemmerer et al. |
| 5,217,453 A | 6/1993 | Wilk |
| 5,220,263 A | 6/1993 | Onishi et al. |
| 5,224,157 A | 6/1993 | Yamada et al. |
| 5,230,023 A | 7/1993 | Nakano |
| 5,231,693 A | 7/1993 | Backes et al. |
| 5,236,432 A | 8/1993 | Matsen et al. |
| 5,262,944 A | 11/1993 | Weisner et al. |
| 5,305,427 A | 4/1994 | Nagata |
| 5,315,287 A | 5/1994 | Sol |
| 5,319,611 A | 6/1994 | Korba |
| 5,341,242 A | 8/1994 | Gilboa et al. |
| 5,341,459 A | 8/1994 | Backes |
| 5,341,854 A | 8/1994 | Zezulka et al. |
| 5,347,306 A | 9/1994 | Nitta |
| 5,347,457 A | 9/1994 | Tanaka et al. |
| 5,350,033 A | 9/1994 | Kraft |
| 5,366,896 A | 11/1994 | Margrey et al. |
| 5,374,879 A | 12/1994 | Pin et al. |
| 5,375,195 A | 12/1994 | Johnston |
| 5,400,068 A | 3/1995 | Ishida et al. |
| 5,417,210 A | 5/1995 | Funda et al. |
| 5,419,008 A | 5/1995 | West |
| 5,436,542 A | 7/1995 | Petelin et al. |
| 5,441,042 A | 8/1995 | Putman |
| 5,441,047 A | 8/1995 | David et al. |
| 5,442,728 A | 8/1995 | Kaufman et al. |
| 5,462,051 A | 10/1995 | Oka et al. |
| 5,486,853 A | 1/1996 | Baxter et al. |
| 5,510,832 A | 4/1996 | Garcia |
| 5,511,147 A | 4/1996 | Abdel-Malek |
| 5,528,289 A | 6/1996 | Cortjens et al. |
| 5,539,741 A | 7/1996 | Barraclough et al. |
| 5,544,649 A | 8/1996 | David et al. |
| 5,550,577 A | 8/1996 | Verbiest et al. |
| 5,553,609 A | 9/1996 | Chen et al. |
| 5,563,998 A | 10/1996 | Yaksich et al. |
| 5,572,229 A | 11/1996 | Fisher |
| 5,572,999 A | 11/1996 | Funda et al. |
| 5,594,859 A | 1/1997 | Palmer et al. |
| 5,600,573 A | 2/1997 | Hendricks et al. |
| 5,617,539 A | 4/1997 | Ludwig et al. |
| 5,619,341 A | 4/1997 | Auyeung et al. |
| 5,623,679 A | 4/1997 | Rivette et al. |
| 5,630,566 A | 5/1997 | Case |
| 5,636,218 A | 6/1997 | Ishikawa et al. |
| 5,652,849 A | 7/1997 | Conway et al. |
| 5,657,246 A | 8/1997 | Hogan et al. |
| 5,659,779 A | 8/1997 | Laird et al. |
| 5,673,082 A | 9/1997 | Wells et al. |
| 5,675,229 A | 10/1997 | Thorne |
| 5,682,199 A | 10/1997 | Lankford |
| 5,684,695 A | 11/1997 | Bauer |
| 5,701,904 A | 12/1997 | Simmons et al. |
| 5,734,805 A | 3/1998 | Isensee et al. |
| 5,739,657 A | 4/1998 | Takayama et al. |
| 5,748,629 A | 5/1998 | Caldara et al. |
| 5,749,058 A | 5/1998 | Hashimoto |
| 5,749,362 A | 5/1998 | Funda et al. |
| 5,754,631 A | 5/1998 | Cave |
| 5,758,079 A | 5/1998 | Ludwig et al. |
| 5,762,458 A | 6/1998 | Wang et al. |
| 5,764,731 A | 6/1998 | Yablon |
| 5,767,897 A | 6/1998 | Howell |
| 5,786,846 A | 7/1998 | Hiroaki |
| 5,787,545 A | 8/1998 | Colens |
| 5,793,365 A | 8/1998 | Tang et al. |
| 5,801,755 A | 9/1998 | Echerer |
| 5,802,494 A | 9/1998 | Kuno |
| 5,836,872 A | 11/1998 | Kenet et al. |
| 5,838,575 A | 11/1998 | Lion |
| 5,844,599 A | 12/1998 | Hildin |
| 5,857,534 A | 1/1999 | Devault et al. |
| 5,867,494 A | 2/1999 | Krishnaswamy et al. |
| 5,867,653 A | 2/1999 | Aras et al. |
| 5,871,451 A | 2/1999 | Unger et al. |
| 5,872,922 A | 2/1999 | Hogan et al. |
| 5,876,325 A | 3/1999 | Mizuno et al. |
| 5,911,036 A | 6/1999 | Wright et al. |
| 5,917,958 A | 6/1999 | Nunally et al. |
| 5,927,423 A | 7/1999 | Wada et al. |
| 5,949,758 A | 9/1999 | Kober |
| 5,954,692 A | 9/1999 | Smith et al. |
| 5,959,423 A | 9/1999 | Nakanishi et al. |
| 5,961,446 A | 10/1999 | Beller et al. |
| 5,966,130 A | 10/1999 | Benman |
| 5,973,724 A | 10/1999 | Riddle |
| 5,974,446 A | 10/1999 | Sonnenreich et al. |
| 5,983,263 A | 11/1999 | Rothrock et al. |
| 5,995,119 A | 11/1999 | Cosatto et al. |
| 5,995,884 A | 11/1999 | Allen et al. |
| 5,999,977 A | 12/1999 | Riddle |
| 6,006,946 A | 12/1999 | Williams et al. |
| 6,031,845 A | 2/2000 | Walding |
| 6,036,812 A | 3/2000 | Williams et al. |
| 6,047,259 A | 4/2000 | Campbell et al. |

(56) References Cited

U.S. PATENT DOCUMENTS

| | | | |
|---|---|---|---|
| 6,091,219 A * | 7/2000 | Maruo | G05B 19/31 318/562 |
| 6,113,343 A | 9/2000 | Goldenberg et al. | |
| 6,133,944 A | 10/2000 | Braun et al. | |
| 6,135,228 A | 10/2000 | Asada et al. | |
| 6,148,100 A | 11/2000 | Anderson et al. | |
| 6,160,582 A | 12/2000 | Hill | |
| 6,170,929 B1 | 1/2001 | Wilson et al. | |
| 6,175,779 B1 | 1/2001 | Barrett | |
| 6,189,034 B1 | 2/2001 | Riddle | |
| 6,201,984 B1 | 3/2001 | Funda et al. | |
| 6,211,903 B1 | 4/2001 | Bullister | |
| 6,219,587 B1 | 4/2001 | Ahlin et al. | |
| 6,232,735 B1 * | 5/2001 | Baba | B25J 9/1689 318/567 |
| 6,233,504 B1 | 5/2001 | Das et al. | |
| 6,233,735 B1 | 5/2001 | Ebihara | |
| 6,250,928 B1 | 6/2001 | Poggio et al. | |
| 6,256,556 B1 | 7/2001 | Zenke | |
| 6,259,806 B1 | 7/2001 | Green | |
| 6,259,956 B1 | 7/2001 | Myers et al. | |
| 6,266,162 B1 | 7/2001 | Okamura et al. | |
| 6,266,577 B1 | 7/2001 | Popp et al. | |
| 6,289,263 B1 | 9/2001 | Mukherjee | |
| 6,292,713 B1 | 9/2001 | Jouppi et al. | |
| 6,292,714 B1 | 9/2001 | Okabayashi Miwa | |
| 6,304,050 B1 | 10/2001 | Skaar et al. | |
| 6,314,631 B1 | 11/2001 | Pryor | |
| 6,317,652 B1 | 11/2001 | Osada | |
| 6,317,953 B1 | 11/2001 | Pryor | |
| 6,321,137 B1 | 11/2001 | De Smet | |
| 6,324,184 B1 | 11/2001 | Hou et al. | |
| 6,324,443 B1 * | 11/2001 | Kurakake | B25J 9/1656 318/568.24 |
| 6,325,756 B1 | 12/2001 | Webb et al. | |
| 6,327,516 B1 | 12/2001 | Zenke | |
| 6,330,486 B1 | 12/2001 | Padula | |
| 6,330,493 B1 | 12/2001 | Takahashi et al. | |
| 6,346,950 B1 | 2/2002 | Jouppi | |
| 6,346,962 B1 | 2/2002 | Goodridge | |
| 6,369,847 B1 | 4/2002 | James et al. | |
| 6,373,855 B1 | 4/2002 | Downing et al. | |
| 6,381,515 B1 | 4/2002 | Inoue et al. | |
| 6,389,329 B1 | 5/2002 | Colens | |
| 6,400,378 B1 | 6/2002 | Snook | |
| 6,408,230 B2 | 6/2002 | Wada | |
| 6,411,055 B1 | 6/2002 | Fujita et al. | |
| 6,430,471 B1 | 8/2002 | Kintou et al. | |
| 6,430,475 B2 | 8/2002 | Okamoto et al. | |
| 6,438,457 B1 | 8/2002 | Yokoo et al. | |
| 6,445,964 B1 | 9/2002 | White et al. | |
| 6,449,762 B1 | 9/2002 | Mcelvain | |
| 6,452,915 B1 | 9/2002 | Jorgensen | |
| 6,457,043 B1 | 9/2002 | Kwak et al. | |
| 6,459,955 B1 | 10/2002 | Bartsch et al. | |
| 6,463,352 B1 | 10/2002 | Tadokoro et al. | |
| 6,463,361 B1 | 10/2002 | Wang et al. | |
| 6,466,844 B1 | 10/2002 | Ikeda et al. | |
| 6,468,265 B1 | 10/2002 | Evans et al. | |
| 6,470,235 B2 | 10/2002 | Kasuga et al. | |
| 6,474,434 B1 | 11/2002 | Bech | |
| 6,480,762 B1 | 11/2002 | Uchikubo et al. | |
| 6,491,701 B2 | 12/2002 | Tierney et al. | |
| 6,496,099 B2 | 12/2002 | Wang et al. | |
| 6,496,755 B2 | 12/2002 | Wallach et al. | |
| 6,501,740 B1 | 12/2002 | Sun et al. | |
| 6,507,773 B2 | 1/2003 | Parker et al. | |
| 6,522,906 B1 | 2/2003 | Salisbury et al. | |
| 6,523,629 B1 | 2/2003 | Buttz et al. | |
| 6,526,332 B2 | 2/2003 | Sakamoto et al. | |
| 6,529,620 B2 | 3/2003 | Thompson | |
| 6,529,765 B1 | 3/2003 | Franck et al. | |
| 6,529,802 B1 | 3/2003 | Kawakita et al. | |
| 6,532,404 B2 | 3/2003 | Colens | |
| 6,535,182 B2 | 3/2003 | Stanton | |
| 6,535,793 B2 | 3/2003 | Allard | |
| 6,540,039 B1 | 4/2003 | Yu et al. | |
| 6,543,899 B2 | 4/2003 | Covannon et al. | |
| 6,549,215 B2 | 4/2003 | Jouppi | |
| 6,563,533 B1 | 5/2003 | Colby | |
| 6,567,038 B1 | 5/2003 | Granot et al. | |
| 6,580,246 B2 | 6/2003 | Jacobs | |
| 6,581,798 B2 | 6/2003 | Liff et al. | |
| 6,584,376 B1 | 6/2003 | Van Kommer | |
| 6,587,750 B2 | 7/2003 | Gerbi et al. | |
| 6,590,604 B1 | 7/2003 | Tucker et al. | |
| 6,594,269 B1 | 7/2003 | Polcyn | |
| 6,594,552 B1 | 7/2003 | Nowlin et al. | |
| 6,597,392 B1 | 7/2003 | Jenkins et al. | |
| 6,602,469 B1 | 8/2003 | Maus et al. | |
| 6,604,019 B2 | 8/2003 | Ahlin et al. | |
| 6,604,021 B2 | 8/2003 | Imai et al. | |
| 6,611,120 B2 | 8/2003 | Song et al. | |
| 6,643,496 B1 | 11/2003 | Shimoyama et al. | |
| 6,646,677 B2 | 11/2003 | Noro et al. | |
| 6,650,748 B1 | 11/2003 | Edwards et al. | |
| 6,666,374 B1 | 12/2003 | Green et al. | |
| 6,667,592 B2 | 12/2003 | Jacobs et al. | |
| 6,674,259 B1 | 1/2004 | Norman et al. | |
| 6,684,129 B2 | 1/2004 | Salisbury et al. | |
| 6,691,000 B2 | 2/2004 | Nagai et al. | |
| 6,693,585 B1 * | 2/2004 | MacLeod | G01S 5/0027 342/357.55 |
| 6,710,797 B1 | 3/2004 | Mcnelley et al. | |
| 6,724,823 B2 | 4/2004 | Rovati et al. | |
| 6,728,599 B2 | 4/2004 | Wang et al. | |
| 6,763,282 B2 | 7/2004 | Glenn et al. | |
| 6,764,373 B1 | 7/2004 | Osawa et al. | |
| 6,769,771 B2 | 8/2004 | Trumbull | |
| 6,781,606 B2 | 8/2004 | Jouppi | |
| 6,784,916 B2 | 8/2004 | Smith | |
| 6,785,589 B2 | 8/2004 | Eggenberger et al. | |
| 6,791,550 B2 | 9/2004 | Goldhor et al. | |
| 6,798,753 B1 | 9/2004 | Doganata et al. | |
| 6,799,065 B1 | 9/2004 | Niemeyer | |
| 6,799,088 B2 | 9/2004 | Wang et al. | |
| 6,804,580 B1 | 10/2004 | Stoddard et al. | |
| 6,804,656 B1 | 10/2004 | Rosenfeld et al. | |
| 6,810,411 B1 | 10/2004 | Coughlin et al. | |
| 6,816,192 B1 | 11/2004 | Nishikawa | |
| 6,816,754 B2 * | 11/2004 | Mukai | B25J 9/1602 29/739 |
| 6,836,703 B2 | 12/2004 | Wang et al. | |
| 6,839,612 B2 | 1/2005 | Sanchez et al. | |
| 6,840,904 B2 | 1/2005 | Goldberg | |
| 6,845,297 B2 | 1/2005 | Allard | |
| 6,852,107 B2 | 2/2005 | Wang et al. | |
| 6,853,878 B2 | 2/2005 | Hirayama et al. | |
| 6,853,880 B2 | 2/2005 | Sakagami et al. | |
| 6,871,117 B2 | 3/2005 | Wang et al. | |
| 6,879,879 B2 | 4/2005 | Jouppi et al. | |
| 6,888,333 B2 * | 5/2005 | Laby | B25J 5/007 180/343 |
| 6,892,112 B2 | 5/2005 | Wang et al. | |
| 6,893,267 B1 | 5/2005 | Yueh | |
| 6,895,305 B2 | 5/2005 | Lathan et al. | |
| 6,898,484 B2 | 5/2005 | Lemelson et al. | |
| 6,914,622 B1 | 7/2005 | Smith et al. | |
| 6,925,357 B2 | 8/2005 | Wang et al. | |
| 6,951,535 B2 | 10/2005 | Ghodoussi et al. | |
| 6,952,470 B1 | 10/2005 | Tioe et al. | |
| 6,957,712 B2 | 10/2005 | Song et al. | |
| 6,958,706 B2 | 10/2005 | Chaco et al. | |
| 6,965,394 B2 | 11/2005 | Gutta et al. | |
| 6,990,112 B1 | 1/2006 | Brent et al. | |
| 6,995,664 B1 | 2/2006 | Darling | |
| 7,007,235 B1 | 2/2006 | Hussein et al. | |
| 7,011,538 B2 | 3/2006 | Chang | |
| 7,015,934 B2 | 3/2006 | Toyama et al. | |
| RE39,080 E | 4/2006 | Johnston | |
| 7,030,757 B2 | 4/2006 | Matsuhira et al. | |
| 7,053,578 B2 | 5/2006 | Diehl et al. | |
| 7,055,210 B2 | 6/2006 | Keppler et al. | |
| 7,058,689 B2 | 6/2006 | Parker et al. | |

(56) References Cited

U.S. PATENT DOCUMENTS

| | | |
|---|---|---|
| 7,092,001 B2 | 8/2006 | Schulz |
| 7,096,090 B1 | 8/2006 | Zweig |
| 7,115,102 B2 | 10/2006 | Abbruscato |
| 7,117,067 B2 | 10/2006 | Mclurkin et al. |
| 7,123,285 B2 | 10/2006 | Smith et al. |
| 7,123,974 B1 | 10/2006 | Hamilton |
| 7,123,991 B2 | 10/2006 | Graf et al. |
| 7,127,325 B2 | 10/2006 | Nagata et al. |
| 7,129,970 B2 | 10/2006 | James et al. |
| 7,133,062 B2 | 11/2006 | Castles et al. |
| 7,142,945 B2 | 11/2006 | Wang et al. |
| 7,142,947 B2 | 11/2006 | Wang et al. |
| 7,151,982 B2 | 12/2006 | Liff et al. |
| 7,154,526 B2 | 12/2006 | Foote et al. |
| 7,155,306 B2 | 12/2006 | Haitin et al. |
| 7,155,309 B2 * | 12/2006 | Peless ............... G05D 1/0219 318/250 |
| 7,156,809 B2 | 1/2007 | Quy |
| 7,158,859 B2 | 1/2007 | Wang et al. |
| 7,158,860 B2 | 1/2007 | Wang et al. |
| 7,158,861 B2 | 1/2007 | Wang et al. |
| 7,161,322 B2 | 1/2007 | Wang et al. |
| 7,162,338 B2 | 1/2007 | Goncalves et al. |
| 7,164,969 B2 | 1/2007 | Wang et al. |
| 7,164,970 B2 | 1/2007 | Wang et al. |
| 7,167,448 B2 | 1/2007 | Wookey et al. |
| 7,171,286 B2 | 1/2007 | Wang et al. |
| 7,174,238 B1 | 2/2007 | Zweig |
| 7,181,455 B2 | 2/2007 | Wookey et al. |
| 7,184,559 B2 | 2/2007 | Jouppi |
| 7,188,000 B2 | 3/2007 | Chiappetta et al. |
| 7,199,790 B2 | 4/2007 | Rosenberg et al. |
| 7,202,851 B2 | 4/2007 | Cunningham et al. |
| 7,206,627 B2 | 4/2007 | Abovitz et al. |
| 7,215,786 B2 | 5/2007 | Nakadai et al. |
| 7,219,364 B2 | 5/2007 | Bolle et al. |
| 7,222,000 B2 | 5/2007 | Wang et al. |
| 7,227,334 B2 | 6/2007 | Yang et al. |
| 7,256,708 B2 | 8/2007 | Rosenfeld et al. |
| 7,262,573 B2 | 8/2007 | Wang et al. |
| 7,283,153 B2 | 10/2007 | Provost et al. |
| 7,289,883 B2 | 10/2007 | Wang et al. |
| 7,292,257 B2 | 11/2007 | Kang et al. |
| 7,292,912 B2 | 11/2007 | Wang et al. |
| 7,305,114 B2 | 12/2007 | Wolff et al. |
| 7,317,685 B1 | 1/2008 | Flott et al. |
| 7,321,807 B2 | 1/2008 | Laski |
| 7,332,890 B2 | 2/2008 | Cohen et al. |
| 7,333,642 B2 | 2/2008 | Green |
| 7,346,429 B2 | 3/2008 | Goldenberg et al. |
| 7,352,153 B2 | 4/2008 | Yan |
| 7,363,121 B1 | 4/2008 | Chen et al. |
| 7,382,399 B1 | 6/2008 | Mccall et al. |
| 7,386,730 B2 | 6/2008 | Uchikubo |
| 7,391,432 B2 | 6/2008 | Terada |
| 7,400,578 B2 | 7/2008 | Guthrie et al. |
| 7,404,140 B2 | 7/2008 | O'Rourke |
| 7,421,470 B2 | 9/2008 | Ludwig et al. |
| 7,430,209 B2 | 9/2008 | Porter |
| 7,432,949 B2 | 10/2008 | Remy et al. |
| 7,433,921 B2 | 10/2008 | Ludwig et al. |
| 7,441,953 B2 | 10/2008 | Banks |
| 7,467,211 B1 | 12/2008 | Herman et al. |
| 7,483,867 B2 | 1/2009 | Ansari et al. |
| 7,492,731 B2 | 2/2009 | Hagendorf |
| 7,510,428 B2 | 3/2009 | Obata et al. |
| 7,523,069 B1 | 4/2009 | Friedl et al. |
| 7,525,281 B2 | 4/2009 | Koyanagi et al. |
| 7,535,486 B2 | 5/2009 | Motomura et al. |
| 7,557,758 B2 | 7/2009 | Rofougaran |
| 7,587,260 B2 | 9/2009 | Bruemmer et al. |
| 7,587,512 B2 | 9/2009 | Ta et al. |
| 7,590,060 B2 | 9/2009 | Miceli |
| 7,593,030 B2 | 9/2009 | Wang et al. |
| 7,599,290 B2 | 10/2009 | Dos Remedios et al. |
| 7,624,166 B2 | 11/2009 | Foote et al. |
| 7,630,314 B2 | 12/2009 | Dos Remedios et al. |
| 7,631,833 B1 | 12/2009 | Ghaleb et al. |
| 7,643,051 B2 | 1/2010 | Sandberg et al. |
| 7,647,320 B2 | 1/2010 | Mok et al. |
| 7,657,560 B1 | 2/2010 | Dirienzo |
| 7,680,038 B1 | 3/2010 | Gourlay |
| 7,693,757 B2 | 4/2010 | Zimmerman |
| 7,698,432 B2 | 4/2010 | Short et al. |
| 7,703,113 B2 | 4/2010 | Dawson |
| 7,719,229 B2 | 5/2010 | Kaneko et al. |
| 7,737,993 B2 | 6/2010 | Kaasila et al. |
| 7,739,383 B1 | 6/2010 | Short et al. |
| 7,756,614 B2 | 7/2010 | Jouppi |
| 7,761,185 B2 | 7/2010 | Wang et al. |
| 7,769,492 B2 | 8/2010 | Wang et al. |
| 7,769,705 B1 | 8/2010 | Luechtefeld |
| 7,774,158 B2 | 8/2010 | Domingues Goncalves et al. |
| 7,813,836 B2 * | 10/2010 | Wang ................. G05D 1/0038 180/169 |
| 7,831,575 B2 | 11/2010 | Trossell et al. |
| 7,835,775 B2 | 11/2010 | Sawayama et al. |
| 7,860,680 B2 | 12/2010 | Arms et al. |
| 7,861,366 B2 | 1/2011 | Hahm et al. |
| 7,885,822 B2 | 2/2011 | Akers et al. |
| 7,890,382 B2 | 2/2011 | Robb et al. |
| 7,912,583 B2 * | 3/2011 | Gutmann ................ G06T 7/593 700/245 |
| RE42,288 E | 4/2011 | Degioanni |
| 7,924,323 B2 | 4/2011 | Walker et al. |
| 7,949,616 B2 | 5/2011 | Levy et al. |
| 7,956,894 B2 | 6/2011 | Akers et al. |
| 7,957,837 B2 | 6/2011 | Ziegler et al. |
| 7,982,763 B2 | 7/2011 | King |
| 7,982,769 B2 | 7/2011 | Jenkins et al. |
| 7,987,069 B2 | 7/2011 | Rodgers et al. |
| 8,077,963 B2 | 12/2011 | Wang et al. |
| 8,116,910 B2 | 2/2012 | Walters et al. |
| 8,126,960 B2 | 2/2012 | Obradovich et al. |
| 8,170,241 B2 | 5/2012 | Roe et al. |
| 8,179,418 B2 | 5/2012 | Wright et al. |
| 8,180,486 B2 | 5/2012 | Saito et al. |
| 8,209,051 B2 | 6/2012 | Wang et al. |
| 8,212,533 B2 | 7/2012 | Ota |
| 8,265,793 B2 | 9/2012 | Cross et al. |
| 8,287,522 B2 | 10/2012 | Moses et al. |
| 8,292,807 B2 | 10/2012 | Perkins et al. |
| 8,320,534 B2 | 11/2012 | Kim et al. |
| 8,340,654 B2 | 12/2012 | Bratton et al. |
| 8,340,819 B2 | 12/2012 | Mangaser et al. |
| 8,348,675 B2 | 1/2013 | Dohrmann |
| 8,374,171 B2 | 2/2013 | Cho et al. |
| 8,400,491 B1 | 3/2013 | Panpaliya et al. |
| 8,401,275 B2 | 3/2013 | Wang et al. |
| 8,423,284 B2 | 4/2013 | O'Shea |
| 8,451,731 B1 | 5/2013 | Lee et al. |
| 8,463,435 B2 | 6/2013 | Herzog et al. |
| 8,503,340 B1 | 8/2013 | Xu |
| 8,515,577 B2 | 8/2013 | Wang et al. |
| 8,527,094 B2 | 9/2013 | Kumar et al. |
| 8,532,860 B2 | 9/2013 | Daly |
| 8,610,786 B2 | 12/2013 | Ortiz |
| 8,612,051 B2 | 12/2013 | Norman et al. |
| 8,639,797 B1 | 1/2014 | Pan et al. |
| 8,670,017 B2 | 3/2014 | Stuart et al. |
| 8,726,454 B2 | 5/2014 | Gilbert et al. |
| 8,836,751 B2 | 9/2014 | Ballantyne et al. |
| 8,849,679 B2 | 9/2014 | Wang et al. |
| 8,849,680 B2 | 9/2014 | Wright et al. |
| 8,861,750 B2 | 10/2014 | Roe et al. |
| 8,897,920 B2 | 11/2014 | Wang et al. |
| 8,902,278 B2 | 12/2014 | Pinter et al. |
| 9,375,843 B2 | 6/2016 | Wang et al. |
| 2001/0002448 A1 | 5/2001 | Wilson et al. |
| 2001/0010053 A1 | 7/2001 | Ben-Shachar et al. |
| 2001/0020200 A1 | 9/2001 | Das et al. |
| 2001/0034475 A1 | 10/2001 | Flach et al. |
| 2001/0034544 A1 | 10/2001 | Mo |

(56) References Cited

U.S. PATENT DOCUMENTS

| | | |
|---|---|---|
| 2001/0037163 A1* | 11/2001 | Allard .................... B25J 9/1689 700/245 |
| 2001/0048464 A1 | 12/2001 | Barnett |
| 2001/0051881 A1 | 12/2001 | Filler |
| 2001/0054071 A1 | 12/2001 | Loeb |
| 2001/0055373 A1 | 12/2001 | Yamashita |
| 2002/0015296 A1 | 2/2002 | Howell et al. |
| 2002/0027597 A1 | 3/2002 | Sachau |
| 2002/0027652 A1* | 3/2002 | Paromtchik .......... G05D 1/0236 356/141.1 |
| 2002/0033880 A1 | 3/2002 | Sul et al. |
| 2002/0038168 A1 | 3/2002 | Kasuga et al. |
| 2002/0044201 A1 | 4/2002 | Alexander et al. |
| 2002/0049517 A1 | 4/2002 | Ruffner |
| 2002/0055917 A1 | 5/2002 | Muraca |
| 2002/0057279 A1* | 5/2002 | Jouppi ................... G06T 3/4038 345/619 |
| 2002/0058929 A1 | 5/2002 | Green |
| 2002/0059587 A1 | 5/2002 | Cofano et al. |
| 2002/0063726 A1 | 5/2002 | Jouppi |
| 2002/0073429 A1 | 6/2002 | Beane et al. |
| 2002/0082498 A1 | 6/2002 | Wendt et al. |
| 2002/0085030 A1 | 7/2002 | Ghani |
| 2002/0095238 A1 | 7/2002 | Ahlin et al. |
| 2002/0095239 A1 | 7/2002 | Wallach et al. |
| 2002/0098879 A1 | 7/2002 | Rheey |
| 2002/0104094 A1 | 8/2002 | Alexander et al. |
| 2002/0106998 A1 | 8/2002 | Presley et al. |
| 2002/0109770 A1 | 8/2002 | Terada |
| 2002/0109775 A1 | 8/2002 | White et al. |
| 2002/0111988 A1 | 8/2002 | Sato |
| 2002/0120362 A1 | 8/2002 | Lathan et al. |
| 2002/0128985 A1 | 9/2002 | Greenwald |
| 2002/0130950 A1 | 9/2002 | James et al. |
| 2002/0133062 A1 | 9/2002 | Arling et al. |
| 2002/0141595 A1 | 10/2002 | Jouppi |
| 2002/0143923 A1 | 10/2002 | Alexander |
| 2002/0177925 A1* | 11/2002 | Onishi .................... B25J 9/1669 700/245 |
| 2002/0183894 A1 | 12/2002 | Wang et al. |
| 2002/0184674 A1 | 12/2002 | Xi et al. |
| 2002/0186243 A1 | 12/2002 | Ellis et al. |
| 2003/0021107 A1 | 1/2003 | Howell et al. |
| 2003/0030397 A1 | 2/2003 | Simmons |
| 2003/0048481 A1 | 3/2003 | Kobayashi et al. |
| 2003/0050733 A1 | 3/2003 | Wang et al. |
| 2003/0050734 A1 | 3/2003 | Lapham |
| 2003/0060808 A1 | 3/2003 | Wilk |
| 2003/0063600 A1 | 4/2003 | Noma et al. |
| 2003/0069752 A1 | 4/2003 | Ledain et al. |
| 2003/0080901 A1 | 5/2003 | Piotrowski |
| 2003/0100892 A1 | 5/2003 | Morley et al. |
| 2003/0104806 A1 | 6/2003 | Ruef et al. |
| 2003/0109267 A1* | 6/2003 | Bulut .................... H04W 64/00 455/457 |
| 2003/0112823 A1 | 6/2003 | Collins et al. |
| 2003/0114962 A1 | 6/2003 | Niemeyer |
| 2003/0120714 A1 | 6/2003 | Wolff et al. |
| 2003/0126361 A1 | 7/2003 | Slater et al. |
| 2003/0135097 A1 | 7/2003 | Wiederhold et al. |
| 2003/0135203 A1 | 7/2003 | Wang et al. |
| 2003/0144579 A1 | 7/2003 | Buss |
| 2003/0144649 A1 | 7/2003 | Ghodoussi et al. |
| 2003/0151658 A1 | 8/2003 | Smith |
| 2003/0152145 A1 | 8/2003 | Kawakita |
| 2003/0171710 A1 | 9/2003 | Bassuk et al. |
| 2003/0174285 A1 | 9/2003 | Trumbull |
| 2003/0180697 A1 | 9/2003 | Kim et al. |
| 2003/0195662 A1 | 10/2003 | Wang et al. |
| 2003/0199000 A1 | 10/2003 | Valkirs et al. |
| 2003/0206242 A1 | 11/2003 | Choi |
| 2003/0212472 A1* | 11/2003 | McKee ................ G05D 1/0274 700/245 |
| 2003/0216833 A1* | 11/2003 | Mukai .................... B25J 9/1602 700/245 |
| 2003/0216834 A1 | 11/2003 | Allard |
| 2003/0220541 A1 | 11/2003 | Salisbury et al. |
| 2003/0220715 A1 | 11/2003 | Kneifel et al. |
| 2003/0231244 A1 | 12/2003 | Bonilla et al. |
| 2003/0232649 A1 | 12/2003 | Gizis et al. |
| 2003/0236590 A1* | 12/2003 | Park ...................... B25J 9/1664 700/245 |
| 2004/0000713 A1* | 1/2004 | Yamashita ........... A61B 5/0002 257/728 |
| 2004/0001197 A1 | 1/2004 | Ko et al. |
| 2004/0001676 A1 | 1/2004 | Colgan et al. |
| 2004/0008138 A1* | 1/2004 | Hockley, Jr. .......... G01S 5/0072 342/357.48 |
| 2004/0010344 A1 | 1/2004 | Hiratsuka et al. |
| 2004/0012362 A1 | 1/2004 | Tsurumi |
| 2004/0013295 A1 | 1/2004 | Sabe et al. |
| 2004/0017475 A1 | 1/2004 | Akers et al. |
| 2004/0019406 A1 | 1/2004 | Wang et al. |
| 2004/0024490 A1 | 2/2004 | Mclurkin et al. |
| 2004/0041904 A1 | 3/2004 | Lapalme et al. |
| 2004/0065073 A1 | 4/2004 | Nash |
| 2004/0068657 A1 | 4/2004 | Alexander et al. |
| 2004/0078219 A1 | 4/2004 | Kaylor et al. |
| 2004/0080610 A1 | 4/2004 | James et al. |
| 2004/0088077 A1 | 5/2004 | Jouppi et al. |
| 2004/0088078 A1 | 5/2004 | Jouppi et al. |
| 2004/0093409 A1 | 5/2004 | Thompson et al. |
| 2004/0095516 A1 | 5/2004 | Rohlicek |
| 2004/0098167 A1 | 5/2004 | Yi et al. |
| 2004/0102167 A1 | 5/2004 | Shim et al. |
| 2004/0107254 A1 | 6/2004 | Ludwig et al. |
| 2004/0107255 A1 | 6/2004 | Ludwig et al. |
| 2004/0117065 A1 | 6/2004 | Wang et al. |
| 2004/0117067 A1 | 6/2004 | Jouppi |
| 2004/0123158 A1 | 6/2004 | Roskind |
| 2004/0135879 A1 | 7/2004 | Stacy et al. |
| 2004/0138547 A1 | 7/2004 | Wang et al. |
| 2004/0143421 A1 | 7/2004 | Wang et al. |
| 2004/0148638 A1 | 7/2004 | Weisman et al. |
| 2004/0150725 A1 | 8/2004 | Taguchi |
| 2004/0153211 A1 | 8/2004 | Kamoto et al. |
| 2004/0157612 A1 | 8/2004 | Kim, II |
| 2004/0162637 A1 | 8/2004 | Wang et al. |
| 2004/0167666 A1 | 8/2004 | Wang et al. |
| 2004/0167668 A1 | 8/2004 | Wang et al. |
| 2004/0168148 A1 | 8/2004 | Goncalves et al. |
| 2004/0170300 A1 | 9/2004 | Jouppi |
| 2004/0172301 A1 | 9/2004 | Mihai et al. |
| 2004/0172306 A1 | 9/2004 | Wohl et al. |
| 2004/0174129 A1 | 9/2004 | Wang et al. |
| 2004/0175684 A1 | 9/2004 | Kaasa et al. |
| 2004/0179714 A1 | 9/2004 | Jouppi |
| 2004/0186623 A1 | 9/2004 | Dooley et al. |
| 2004/0189700 A1 | 9/2004 | Mandavilli et al. |
| 2004/0201602 A1 | 10/2004 | Mody et al. |
| 2004/0205664 A1 | 10/2004 | Prendergast |
| 2004/0215490 A1 | 10/2004 | Duchon et al. |
| 2004/0218099 A1 | 11/2004 | Washington |
| 2004/0222638 A1 | 11/2004 | Bednyak |
| 2004/0224676 A1 | 11/2004 | Iseki |
| 2004/0230340 A1 | 11/2004 | Fukuchi et al. |
| 2004/0240981 A1 | 12/2004 | Dothan et al. |
| 2004/0241981 A1 | 12/2004 | Doris et al. |
| 2004/0260790 A1 | 12/2004 | Balloni et al. |
| 2005/0003330 A1 | 1/2005 | Asgarinejad et al. |
| 2005/0004708 A1 | 1/2005 | Goldenberg et al. |
| 2005/0007445 A1 | 1/2005 | Foote et al. |
| 2005/0013149 A1 | 1/2005 | Trossell |
| 2005/0021182 A1 | 1/2005 | Wang et al. |
| 2005/0021183 A1 | 1/2005 | Wang et al. |
| 2005/0021187 A1 | 1/2005 | Wang et al. |
| 2005/0021309 A1 | 1/2005 | Alexander et al. |
| 2005/0024485 A1 | 2/2005 | Castles et al. |
| 2005/0027567 A1 | 2/2005 | Taha |
| 2005/0027794 A1 | 2/2005 | Decker |
| 2005/0028221 A1 | 2/2005 | Liu et al. |
| 2005/0035862 A1 | 2/2005 | Wildman et al. |

(56) References Cited

U.S. PATENT DOCUMENTS

| | | |
|---|---|---|
| 2005/0038416 A1 | 2/2005 | Wang et al. |
| 2005/0038564 A1 | 2/2005 | Burick |
| 2005/0049898 A1 | 3/2005 | Hirakawa |
| 2005/0052527 A1 | 3/2005 | Remy et al. |
| 2005/0060211 A1 | 3/2005 | Xiao et al. |
| 2005/0065435 A1 | 3/2005 | Rauch et al. |
| 2005/0065438 A1 | 3/2005 | Miller |
| 2005/0065659 A1 | 3/2005 | Tanaka et al. |
| 2005/0065813 A1 | 3/2005 | Mishelevich et al. |
| 2005/0071046 A1 | 3/2005 | Miyazaki et al. |
| 2005/0073575 A1 | 4/2005 | Thacher et al. |
| 2005/0078816 A1 | 4/2005 | Sekiguchi et al. |
| 2005/0083011 A1 | 4/2005 | Yang et al. |
| 2005/0099493 A1 | 5/2005 | Chew |
| 2005/0104964 A1 | 5/2005 | Bovyrin et al. |
| 2005/0110867 A1 | 5/2005 | Schulz |
| 2005/0122390 A1 | 6/2005 | Wang et al. |
| 2005/0125083 A1 | 6/2005 | Kiko |
| 2005/0125098 A1 | 6/2005 | Wang et al. |
| 2005/0149364 A1 | 7/2005 | Ombrellaro |
| 2005/0152447 A1 | 7/2005 | Jouppi et al. |
| 2005/0152565 A1 | 7/2005 | Jouppi et al. |
| 2005/0154265 A1 | 7/2005 | Miro et al. |
| 2005/0168568 A1 | 8/2005 | Jouppi |
| 2005/0182322 A1 | 8/2005 | Grispo |
| 2005/0192721 A1 | 9/2005 | Jouppi |
| 2005/0204438 A1 | 9/2005 | Wang et al. |
| 2005/0212478 A1 | 9/2005 | Takenaka |
| 2005/0219356 A1 | 10/2005 | Smith et al. |
| 2005/0225634 A1 | 10/2005 | Brunetti et al. |
| 2005/0231156 A1 | 10/2005 | Yan |
| 2005/0231586 A1 | 10/2005 | Rodman et al. |
| 2005/0232647 A1 | 10/2005 | Takenaka |
| 2005/0234592 A1 | 10/2005 | Mcgee et al. |
| 2005/0264649 A1 | 12/2005 | Chang |
| 2005/0267826 A1 | 12/2005 | Levy et al. |
| 2005/0283414 A1 | 12/2005 | Fernandes et al. |
| 2005/0286759 A1 | 12/2005 | Zitnick et al. |
| 2006/0007943 A1 | 1/2006 | Fellman |
| 2006/0010028 A1 | 1/2006 | Sorensen |
| 2006/0013263 A1 | 1/2006 | Fellman |
| 2006/0013469 A1 | 1/2006 | Wang et al. |
| 2006/0013488 A1 | 1/2006 | Inoue |
| 2006/0014388 A1 | 1/2006 | Lur et al. |
| 2006/0020694 A1 | 1/2006 | Nag et al. |
| 2006/0029065 A1 | 2/2006 | Fellman |
| 2006/0047365 A1 | 3/2006 | Ghodoussi et al. |
| 2006/0048286 A1 | 3/2006 | Donato |
| 2006/0052676 A1 | 3/2006 | Wang et al. |
| 2006/0052684 A1 | 3/2006 | Takahashi et al. |
| 2006/0056655 A1 | 3/2006 | Wen et al. |
| 2006/0056837 A1 | 3/2006 | Vapaakoski |
| 2006/0064212 A1 | 3/2006 | Thorne |
| 2006/0066609 A1 | 3/2006 | Iodice et al. |
| 2006/0071797 A1 | 4/2006 | Rosenfeld et al. |
| 2006/0074525 A1 | 4/2006 | Close et al. |
| 2006/0074719 A1 | 4/2006 | Horner |
| 2006/0082642 A1 | 4/2006 | Wang et al. |
| 2006/0087746 A1 | 4/2006 | Lipow |
| 2006/0095158 A1 | 5/2006 | Lee et al. |
| 2006/0095170 A1 | 5/2006 | Yang et al. |
| 2006/0098573 A1 | 5/2006 | Beer et al. |
| 2006/0103659 A1 | 5/2006 | Karandikar et al. |
| 2006/0104279 A1 | 5/2006 | Fellman et al. |
| 2006/0106493 A1 | 5/2006 | Niemeyer et al. |
| 2006/0122482 A1 | 6/2006 | Mariotti et al. |
| 2006/0125356 A1 | 6/2006 | Meek et al. |
| 2006/0142983 A1 | 6/2006 | Sorensen et al. |
| 2006/0149418 A1 | 7/2006 | Anvari |
| 2006/0161136 A1 | 7/2006 | Anderson |
| 2006/0161303 A1 | 7/2006 | Wang et al. |
| 2006/0164546 A1 | 7/2006 | Adachi |
| 2006/0171515 A1 | 8/2006 | Hintermeister et al. |
| 2006/0173708 A1 | 8/2006 | Vining et al. |
| 2006/0173712 A1 | 8/2006 | Joubert |
| 2006/0178559 A1 | 8/2006 | Kumar |
| 2006/0178776 A1 | 8/2006 | Feingold et al. |
| 2006/0178777 A1* | 8/2006 | Park ................... B25J 9/0003 700/245 |
| 2006/0189393 A1 | 8/2006 | Edery |
| 2006/0195569 A1 | 8/2006 | Barker |
| 2006/0224781 A1 | 10/2006 | Tsao et al. |
| 2006/0247045 A1 | 11/2006 | Jeong et al. |
| 2006/0259193 A1 | 11/2006 | Wang et al. |
| 2006/0268704 A1 | 11/2006 | Ansari et al. |
| 2006/0271238 A1 | 11/2006 | Choi et al. |
| 2006/0271400 A1 | 11/2006 | Clements et al. |
| 2006/0293788 A1 | 12/2006 | Pogodin |
| 2007/0021871 A1 | 1/2007 | Wang et al. |
| 2007/0025711 A1 | 2/2007 | Marcus |
| 2007/0046237 A1 | 3/2007 | Lakshmanan et al. |
| 2007/0050937 A1 | 3/2007 | Song et al. |
| 2007/0064092 A1 | 3/2007 | Sandbeg et al. |
| 2007/0078566 A1 | 4/2007 | Wang et al. |
| 2007/0093279 A1 | 4/2007 | Janik |
| 2007/0112700 A1 | 5/2007 | Den et al. |
| 2007/0116152 A1 | 5/2007 | Thesling |
| 2007/0117516 A1 | 5/2007 | Saidi et al. |
| 2007/0120965 A1 | 5/2007 | Sandberg et al. |
| 2007/0122783 A1 | 5/2007 | Habashi |
| 2007/0133407 A1 | 6/2007 | Choi et al. |
| 2007/0135967 A1 | 6/2007 | Jung et al. |
| 2007/0142964 A1 | 6/2007 | Abramson |
| 2007/0170886 A1 | 7/2007 | Plishner |
| 2007/0176060 A1 | 8/2007 | White et al. |
| 2007/0188615 A1* | 8/2007 | Beniyama ............. G05D 1/0246 348/207.99 |
| 2007/0192910 A1 | 8/2007 | Vu et al. |
| 2007/0197896 A1 | 8/2007 | Moll et al. |
| 2007/0198128 A1 | 8/2007 | Ziegler et al. |
| 2007/0198130 A1 | 8/2007 | Wang et al. |
| 2007/0199108 A1 | 8/2007 | Angle et al. |
| 2007/0216347 A1 | 9/2007 | Kaneko et al. |
| 2007/0226949 A1 | 10/2007 | Hahm et al. |
| 2007/0250212 A1 | 10/2007 | Halloran et al. |
| 2007/0255706 A1 | 11/2007 | Iketani et al. |
| 2007/0262884 A1 | 11/2007 | Goncalves et al. |
| 2007/0273751 A1 | 11/2007 | Sachau |
| 2007/0290040 A1 | 12/2007 | Wurman et al. |
| 2007/0291109 A1 | 12/2007 | Wang et al. |
| 2007/0291128 A1 | 12/2007 | Wang et al. |
| 2008/0009969 A1 | 1/2008 | Bruemmer et al. |
| 2008/0011904 A1 | 1/2008 | Cepollina et al. |
| 2008/0027591 A1 | 1/2008 | Lenser et al. |
| 2008/0033641 A1 | 2/2008 | Medalia |
| 2008/0045804 A1 | 2/2008 | Williams |
| 2008/0051985 A1 | 2/2008 | D' Andrea et al. |
| 2008/0065268 A1 | 3/2008 | Wang et al. |
| 2008/0082211 A1 | 4/2008 | Wang et al. |
| 2008/0086241 A1 | 4/2008 | Phillips et al. |
| 2008/0091340 A1 | 4/2008 | Milstein et al. |
| 2008/0126132 A1 | 5/2008 | Warner et al. |
| 2008/0133052 A1 | 6/2008 | Jones et al. |
| 2008/0161969 A1 | 7/2008 | Lee et al. |
| 2008/0174570 A1 | 7/2008 | Jobs et al. |
| 2008/0201016 A1 | 8/2008 | Finlay |
| 2008/0201017 A1 | 8/2008 | Wang et al. |
| 2008/0215987 A1 | 9/2008 | Alexander et al. |
| 2008/0229531 A1 | 9/2008 | Takida |
| 2008/0232763 A1 | 9/2008 | Brady |
| 2008/0255703 A1 | 10/2008 | Wang et al. |
| 2008/0263451 A1 | 10/2008 | Portele et al. |
| 2008/0263628 A1 | 10/2008 | Norman et al. |
| 2008/0267069 A1 | 10/2008 | Thielman et al. |
| 2008/0269949 A1 | 10/2008 | Norman et al. |
| 2008/0281467 A1 | 11/2008 | Pinter |
| 2008/0306375 A1 | 12/2008 | Sayler et al. |
| 2009/0030552 A1 | 1/2009 | Nakadai et al. |
| 2009/0044334 A1 | 2/2009 | Parsell et al. |
| 2009/0049640 A1 | 2/2009 | Lee et al. |
| 2009/0055023 A1 | 2/2009 | Walters et al. |
| 2009/0070135 A1 | 3/2009 | Parida et al. |
| 2009/0086013 A1 | 4/2009 | Thapa |
| 2009/0102919 A1 | 4/2009 | Zamierowski et al. |

(56) References Cited

U.S. PATENT DOCUMENTS

| | | |
|---|---|---|
| 2009/0105882 A1 | 4/2009 | Wang et al. |
| 2009/0106679 A1 | 4/2009 | Anzures et al. |
| 2009/0122699 A1 | 5/2009 | Alperovitch et al. |
| 2009/0125147 A1 | 5/2009 | Wang et al. |
| 2009/0144425 A1 | 6/2009 | Marr et al. |
| 2009/0164255 A1 | 6/2009 | Menschik et al. |
| 2009/0164657 A1 | 6/2009 | Li et al. |
| 2009/0171170 A1 | 7/2009 | Li et al. |
| 2009/0177323 A1 | 7/2009 | Ziegler et al. |
| 2009/0177641 A1 | 7/2009 | Raghavan |
| 2009/0237317 A1 | 9/2009 | Rofougaran |
| 2009/0240371 A1 | 9/2009 | Wang et al. |
| 2009/0248200 A1 | 10/2009 | Root |
| 2009/0259339 A1 | 10/2009 | Wright et al. |
| 2010/0010672 A1 | 1/2010 | Wang et al. |
| 2010/0010673 A1 | 1/2010 | Wang et al. |
| 2010/0017046 A1 | 1/2010 | Cheung et al. |
| 2010/0019715 A1 | 1/2010 | Roe et al. |
| 2010/0026239 A1 | 2/2010 | Li et al. |
| 2010/0030578 A1 | 2/2010 | Siddique et al. |
| 2010/0051596 A1 | 3/2010 | Diedrick et al. |
| 2010/0063848 A1 | 3/2010 | Kremer et al. |
| 2010/0066804 A1 | 3/2010 | Shoemake et al. |
| 2010/0070079 A1 | 3/2010 | Mangaser et al. |
| 2010/0073490 A1 | 3/2010 | Wang et al. |
| 2010/0076600 A1 | 3/2010 | Cross et al. |
| 2010/0085874 A1 | 4/2010 | Noy et al. |
| 2010/0088232 A1 | 4/2010 | Gale |
| 2010/0115418 A1 | 5/2010 | Wang et al. |
| 2010/0116566 A1 | 5/2010 | Ohm et al. |
| 2010/0131103 A1 | 5/2010 | Herzog et al. |
| 2010/0145479 A1 | 6/2010 | Griffiths |
| 2010/0157825 A1 | 6/2010 | Anderlind et al. |
| 2010/0171826 A1 | 7/2010 | Hamilton et al. |
| 2010/0191375 A1 | 7/2010 | Wright et al. |
| 2010/0228249 A1 | 9/2010 | Mohr et al. |
| 2010/0268383 A1 | 10/2010 | Wang et al. |
| 2010/0278086 A1 | 11/2010 | Pochiraju et al. |
| 2010/0286905 A1 | 11/2010 | Goncalves et al. |
| 2010/0301679 A1 | 12/2010 | Murray et al. |
| 2010/0323783 A1 | 12/2010 | Nonaka et al. |
| 2011/0022705 A1 | 1/2011 | Yellamraju et al. |
| 2011/0050841 A1 | 3/2011 | Wang et al. |
| 2011/0071675 A1 | 3/2011 | Wells et al. |
| 2011/0071702 A1 | 3/2011 | Wang et al. |
| 2011/0072114 A1 | 3/2011 | Hoffert et al. |
| 2011/0153198 A1 | 6/2011 | Kokkas et al. |
| 2011/0172822 A1 | 7/2011 | Ziegler et al. |
| 2011/0187875 A1 | 8/2011 | Sanchez et al. |
| 2011/0190930 A1 | 8/2011 | Hanrahan et al. |
| 2011/0193949 A1 | 8/2011 | Nambakam et al. |
| 2011/0195701 A1 | 8/2011 | Cook et al. |
| 2011/0213210 A1 | 9/2011 | Temby et al. |
| 2011/0218674 A1 | 9/2011 | Stuart et al. |
| 2011/0245973 A1* | 10/2011 | Wang .................... G05D 1/0038 700/259 |
| 2011/0280551 A1 | 11/2011 | Sammon |
| 2011/0292193 A1 | 12/2011 | Wang et al. |
| 2011/0301759 A1 | 12/2011 | Wang et al. |
| 2011/0306400 A1 | 12/2011 | Nguyen |
| 2012/0023506 A1 | 1/2012 | Maeckel et al. |
| 2012/0036484 A1 | 2/2012 | Zhang et al. |
| 2012/0059946 A1 | 3/2012 | Wang |
| 2012/0072023 A1 | 3/2012 | Ota |
| 2012/0072024 A1 | 3/2012 | Wang et al. |
| 2012/0092157 A1 | 4/2012 | Tran |
| 2012/0095352 A1 | 4/2012 | Tran |
| 2012/0113856 A1 | 5/2012 | Krishnaswamy |
| 2012/0191246 A1 | 7/2012 | Roe et al. |
| 2012/0191464 A1 | 7/2012 | Stuart et al. |
| 2012/0203731 A1 | 8/2012 | Nelson et al. |
| 2012/0291809 A1 | 11/2012 | Kuhe et al. |
| 2013/0250938 A1 | 9/2013 | Anandakumar et al. |
| 2014/0047022 A1 | 2/2014 | Chan et al. |
| 2014/0085543 A1 | 3/2014 | Hartley et al. |
| 2014/0135990 A1 | 5/2014 | Stuart et al. |
| 2014/0139616 A1 | 5/2014 | Pinter et al. |
| 2014/0155755 A1 | 6/2014 | Pinter et al. |

FOREIGN PATENT DOCUMENTS

| | | |
|---|---|---|
| CN | 1404695 A | 3/2003 |
| CN | 1554193 A | 12/2004 |
| CN | 1554985 A | 12/2004 |
| CN | 1561923 A | 1/2005 |
| CN | 1743144 A | 3/2006 |
| CN | 101049017 A | 10/2007 |
| CN | 101106939 A | 1/2008 |
| CN | 101151614 A | 3/2008 |
| CN | 100407729 C | 7/2008 |
| CN | 101390098 A | 3/2009 |
| CN | 101507260 A | 8/2009 |
| CN | 101730894 A | 6/2010 |
| CN | 101866396 A | 10/2010 |
| CN | 101978365 A | 2/2011 |
| CN | 102203759 A | 9/2011 |
| CN | 101106939 B | 11/2011 |
| EP | 466492 A2 | 1/1992 |
| EP | 488673 A2 | 6/1992 |
| EP | 981905 B1 | 1/2002 |
| EP | 1262142 A2 | 12/2002 |
| EP | 1304872 A1 | 4/2003 |
| EP | 1536660 A2 | 6/2005 |
| EP | 1573406 A2 | 9/2005 |
| EP | 1594660 A2 | 11/2005 |
| EP | 1763243 A2 | 3/2007 |
| EP | 1791464 A2 | 6/2007 |
| EP | 1800476 A2 | 6/2007 |
| EP | 1819108 A2 | 8/2007 |
| EP | 1856644 A2 | 11/2007 |
| EP | 1536660 A3 | 4/2008 |
| EP | 1928310 A2 | 6/2008 |
| EP | 1232610 B1 | 1/2009 |
| EP | 2027716 A2 | 2/2009 |
| EP | 2145274 A1 | 1/2010 |
| EP | 2214111 A2 | 8/2010 |
| EP | 2263158 A2 | 12/2010 |
| EP | 2300930 A1 | 3/2011 |
| EP | 2342651 A1 | 7/2011 |
| GB | 2431261 A | 4/2007 |
| JP | 7-194609 A | 8/1995 |
| JP | 7-213753 A | 8/1995 |
| JP | 7-248823 A | 9/1995 |
| JP | 7-257422 A | 10/1995 |
| JP | 8-084328 A | 3/1996 |
| JP | 8-320727 A | 12/1996 |
| JP | 9-267276 A | 10/1997 |
| JP | 10-79097 A | 3/1998 |
| JP | 10-288689 A | 10/1998 |
| JP | 11-220706 A | 8/1999 |
| JP | 2000-032319 A | 1/2000 |
| JP | 2000-049800 A | 2/2000 |
| JP | 2000-079587 A | 3/2000 |
| JP | 2000-196876 A | 7/2000 |
| JP | 2001-125641 A | 5/2001 |
| JP | 2001-147718 A | 5/2001 |
| JP | 2001-179663 A | 7/2001 |
| JP | 2001-188124 A | 7/2001 |
| JP | 2001-198865 A | 7/2001 |
| JP | 2001-198868 A | 7/2001 |
| JP | 2001-199356 A | 7/2001 |
| JP | 2002-000574 A | 1/2002 |
| JP | 2002-046088 A | 2/2002 |
| JP | 2002-101333 A | 4/2002 |
| JP | 2002-112970 A | 4/2002 |
| JP | 2002-235423 A | 8/2002 |
| JP | 2002-305743 A | 10/2002 |
| JP | 2002-321180 A | 11/2002 |
| JP | 2002-355779 A | 12/2002 |
| JP | 2004-181229 A | 7/2004 |
| JP | 2004-524824 T | 8/2004 |
| JP | 2004-261941 A | 9/2004 |
| JP | 2004-289379 A | 10/2004 |
| JP | 2005-028066 A | 2/2005 |

(56) References Cited

FOREIGN PATENT DOCUMENTS

| | | | |
|---|---|---|---|
| JP | 2005-059170 A | 3/2005 | |
| JP | 2005-111083 A | 4/2005 | |
| JP | 2006-508806 A | 3/2006 | |
| JP | 2006-109094 A | 4/2006 | |
| JP | 2006-224294 A | 8/2006 | |
| JP | 2006-246438 A | 9/2006 | |
| JP | 2007-007040 A | 1/2007 | |
| JP | 2007-081646 A | 3/2007 | |
| JP | 2007-232208 A | 9/2007 | |
| JP | 2007-316966 A | 12/2007 | |
| JP | 2009-125133 A | 6/2009 | |
| JP | 2010-064154 A | 3/2010 | |
| JP | 2010-532109 A | 9/2010 | |
| JP | 2010-246954 A | 11/2010 | |
| KR | 2006-0037979 A | 5/2006 | |
| KR | 2009-0012542 A | 2/2009 | |
| KR | 2010-0019479 A | 2/2010 | |
| KR | 2010-0139037 A | 12/2010 | |
| WO | 93/06690 A1 | 4/1993 | |
| WO | 97/42761 A1 | 11/1997 | |
| WO | 1998/51078 A1 | 11/1998 | |
| WO | 99/67067 A1 | 12/1999 | |
| WO | 2000/025516 A1 | 5/2000 | |
| WO | 2000/033726 A1 | 6/2000 | |
| WO | 01/31861 A1 | 5/2001 | |
| WO | 2003/077745 A1 | 9/2003 | |
| WO | 2004/008738 A1 | 1/2004 | |
| WO | 2004/012018 A2 | 2/2004 | |
| WO | 2004/075456 A2 | 9/2004 | |
| WO | 2006/012797 A1 | 2/2006 | |
| WO | 2006/044847 A2 | 4/2006 | |
| WO | 2006/078611 A2 | 7/2006 | |
| WO | 2007/041295 A2 | 4/2007 | |
| WO | 2007/041038 A3 | 6/2007 | |
| WO | 2008/100272 A2 | 8/2008 | |
| WO | 2008/100272 A3 | 10/2008 | |
| WO | 2009/117274 A2 | 9/2009 | |
| WO | 2009/128997 A1 | 10/2009 | |
| WO | 2009/145958 A2 | 12/2009 | |
| WO | 2010/006205 A1 | 1/2010 | |
| WO | 2010/006211 A1 | 1/2010 | |
| WO | 2010/033666 A1 | 3/2010 | |
| WO | 2010/047881 A1 | 4/2010 | |
| WO | 2010/062798 A1 | 6/2010 | |
| WO | 2010/065257 A1 | 6/2010 | |
| WO | 2010/120407 A1 | 10/2010 | |
| WO | 2011/028589 A2 | 3/2011 | |
| WO | 2011/028589 A3 | 4/2011 | |
| WO | 2011/097130 A2 | 8/2011 | |
| WO | 2011/097132 A2 | 8/2011 | |
| WO | 2011/109336 A2 | 9/2011 | |
| WO | 2011/097132 A3 | 12/2011 | |
| WO | 2011/149902 A2 | 12/2011 | |

OTHER PUBLICATIONS

Appeal from the U.S. District Court for the Central District of California in case No. 11-cv-9185, Judge Percy Anderson, Joint Appendix, vol. I of IV, Jun. 24, 2013, pp. A1-A6357.
Appeal from the U.S. District Court for the Central District of California in case No. 11-cv-9185, Judge Percy Anderson, Joint Appendix, vol. II of IV, Jun. 24, 2013, pp. A6849-A10634.
Appeal from the U.S. District Court for the Central District of California in case No. 11-cv-9185, Judge Percy Anderson, Joint Appendix, vol. III of IV, Jun. 24, 2013, pp. A10654-A15517.
Appeal from the U.S. District Court for the Central District of California in case No. 11-cv-9185, Judge Percy Anderson, Joint Appendix, vol. IV of IV, Jun. 24, 2013, pp. A15677-A18127.
Appeal from the U.S. District Court for the Central District of California in No. 11-CV-9185, Judge Percy Anderson, May 9, 2014, pp. 1-48.
Civil Minutes-General: Case No. CV 11-9185PA (AJWx), *InTouch Tech., Inc. v. VGO Commons, Inc.*, Sep. 10, 2012, 7 pages.
Defendant VGO Communications, Inc.'s Invalidity Contentions Pursuant to the Feb. 27, 2012 Civil Minute Order, May 2, 2012, 143 pages.
Defendant-Counterclaimant VGO Communications, Inc.'s Supplemental Invalidity Contentions Pursuant to the Feb. 27, 2012 Civil Minute Order, May 14, 2012, 228 pages.
"Google translation of: Innovations Report", From research project to television star: Care-O-bot in ZDF series, available online at <http://www.innovations-report.de/specials/printa.php?id=5157>, Sep. 28, 2001, 2 pages.
"Magne Charge", Smart Power for Electric Vehicles, Aug. 26, 1997, 2 pages.
"More Online Robots: Robots that Manipulate", available online at <http://ford.ieor.berkeley.edu/ir/robots_a2.html>, Retrieved on Nov. 23, 2010, Aug. 2001, 2 pages.
"MPEG File Format Summary", available online at <http://www.fileformat.info/format/mpeg/egff.htm>, Feb. 1, 2001, 8 pages.
"Nomad Scout Language Reference Manual", Nomadic Technologies, Software Version 2.7, Part No. DOC00002, Jul. 12, 1999, 47 pages.
"Nomad Scout User's Manual", Nomadic Technologies, Software Version 2.7, Part No. DOC00004, Jul. 12, 1999, pp. 1-59.
Opening Brief for Plaintiff-Appellant InTouch Technologies, Inc., Appeal from the U.S. District Court for the Central District of California in Case No. 11-cv-9185, Judge Percy Anderson, Apr. 12, 2013, 187 pages.
PictureTel Adds New Features and Functionality to Its Award-Winning Live200 Desktop Videoconferencing System, PR Newswire Association, LLC, Gale, Cengage Learning, Jun. 13, 1997, 5 pages.
Reply Brief for Defendant-Appellee VGO Communications, Inc., Appeal from the U.S. District Court for the Central District of California, in Case No. 2:11-cv-9185, Judge Percy Anderson, May 28, 2013, 75 pages.
Reply Brief for Plaintiff-Appellant InTouch Technologies, Inc., Appeal from the U.S. District Court for the Central District of California in Case No. 11-cv-9185, Judge Percy Anderson, Jun. 14, 2013, 39 pages.
"Robart I, II, III", Spawar, Systems Center Pacific, 1998, 8 pages.
Using your Infrared Cell Phone Camera, available online at <http://www.catsdomain.com/xray/about.htm>, Courtesy of Internet Wayback Machine, Jan. 30, 2010, 4 pages.
Ivanova, Natali, "Master's Thesis: Internet Based Interface for Control of a Mobile Robot", Department of Numerical Analysis and Computer Science, 2003, 59 pages.
Jacobs et al., "Applying Telemedicine to Outpatient Physical Therapy", AMIA, Annual Symposium Proceedings, 2002, 1 page.
Jenkins et al., "Telehealth Advancing Nursing Practice", Nursing Outlook, vol. 49, No. 2, Mar. 2001, pp. 100-105.
Johanson, Mathias, "Supporting Video-Mediated Communication Over the Internet", Department of Computer Engineering, Chalmers University of Technology, Gothenburg, Sweden, 2003, 222 pages.
ACM Digital Library Record, "Autonomous Robots vol. 11 Issue 1", available online at <http://dl.acm.org/citation.cfm?id=591550&picked=prox&cfid=360891374&cftoken=35225929>, Jul. 2001, 2 pages.
Active Media, Inc., "Saphira Software Manual", Saphira Version 5.3, 1997, 105 pages.
Activmedia Robotics, "Pioneer 2/PeopleBot TM", Operations Manual, Version 9, Oct. 2001, 78 pages.
Adams, Chris, "Simulation of Adaptive Behavior (SAB'02)", Mobile Robotics Research Group, The Seventh International Conference, retrieved on Jan. 22, 2014, available online at <http://www.dai.ed.ac.uk/groups/mrg/MRG.html>, Aug. 4-11, 2002, 1 page.
Ando et al., "A Multimedia Self-service Terminal with Conferencing Functions", Robot and Human Communication, Tokyo, Proceedings of 4th IEEE International Workshop, Jul. 5-7, 1995, pp. 357-362.
Android Amusement Corp., "What Marketing Secret Renting Robots from Android Amusement Corp!", (Advertisement), 1982, 1 page.
Apple Inc., "I Phone", iPhone Series, XP002696350, Sep. 21, 2012, pp. 1-29.

(56) References Cited

OTHER PUBLICATIONS

Applebome, Peter, "Planning Domesticated Robots for Tomorrow's Household", New York Times, available online at <http://www.theoldrobots.com/images17/dc17.jpg>, Mar. 4, 1982, pp. 21 and 23.
Bar-Cohen et al., "Virtual Reality Robotic Telesurgery Simulations Using MEMICA Haptic System", Proceedings of SPIE's 8th Annual International Symposium on Smart Structures and Materials, Mar. 5-8, 2001, pp. 1-7.
Barrett, Rick, "Video Conferencing Business Soars as Companies Cut Travel; Some Travel Cuts Are Permanent", available online at <http://www.ivci.com/international_videoconferencing_news_videoconferencing_news_19.html>, May 13, 2002, 2 pages.
Bartholomew, "Pharmacy Apothecary", available online at <http://classes.bnf.fr/ema/grands/034.htm>, retrieved on Jul. 26, 2012, 2 pages.
Bauer et al., "Remote Telesurgical Mentoring: Feasibility and Efficacy", IEEE, Proceedings of the 33rd Hawaii International Conference on System Sciences, 2000, pp. 1-9.
Bauer, Jeffrey C., "Service Robots in Health Care: The Evolution of Mechanical Solutions to Human Resource Problems", Bon Secours Health System Inc., Technology Early Warning System(TEWS), Future of Service Robots in Health Care, Jun. 2003, pp. 1-10.
Bischoff, Rainer, "Design Concept and Realization of the Humanoid Service Robot HERMES", Field and Service Robotics, Springer, 1998, pp. 485-492.
Blackwell, Gerry, "Video: A Wireless LAN Killer App?", available online at <http://www.wi-fiplanet.com/columns/article.php/1010261/Video-A-Wireless-LAN-Killer>, Apr. 16, 2002, 4 pages.
Blaer et al., "TopBot: Automated Network Topology Detection With a Mobile Robot", IEEE, Proceedings of the 2003 International Conference on Robotics 7 Automation, Taipei, Taiwan, Sep. 14-19, 2003, pp. 1582-1587.
Bradner, S., "The Internet Standards Process—Revision 3", Network Working Group, Request for Comments: 2026, BCP: 9, Obsoletes: 1602, Category: Best Current Practice, Oct. 1996, pp. 1-36.
Brenner, Pablo, "A technical tutorial on the IEEE 802.11 protocol", Breezecom Wireless Communications, 1997, pp. 1-24.
Breslow et al., "Effect of a Multiple-Site Intensive Care Unit Telemedicine Program on Clinical and Economic Outcome an Alternative Paradigm for Intensivist Staffing", Critical Care Med, vol. 32, No. 1, Jan. 2004, pp. 31-38.
Brooks, Rodney, "A Robust Layered Control System for a Mobile Robot", IEEE, Journal of Robotics and Automation, vol. 2, No. 1, Mar. 1986, pp. 14-23.
Brooks, Rodney Allen, "Remote Presence", Abstracts from Flesh & Machines, How Robots Will Change Us, Feb. 2002, pp. 131-147.
Celi et al., "The eICU: It's Not Just Telemedicine", Critical Care Medicine vol. 29, No. 8 (Supplement), Aug. 2001, pp. 183-189.
Cheetham et al., "Interface Development for a Child's Video Conferencing Robot", available online at <www.ryerson.ca/pebbles/publications/paper-iea200hfes-last.pdf>, 2000, 4 pages.
Christensen et al., "BeeSoft User's Guide and Reference", Robots for the Real World™, Real World Interface, Inc ., Sep. 26, 1997, 203 pages.
Chu et al., "Detection of Target Mobile Signal Strength", Technical Development, Motorola Inc, Jan. 1999, pp. 205-206.
Cleary et al., "State of the Art in Surgical Robotics: Clinical Applications and Technology Challenges", Feb. 24, 2002, pp. 1-26.
CMU Course 16X62, "Robot user's manual", (describing the Nomad Scout), Carnegie Mellon University, Feb. 1, 2001, 11 pages.
CNN, "Floating 'Droids' to Roam Space Corridors of the Future", Available online at <http://edition.cnn.com/2000/TECH/space/01/12/psa/>, Jan. 12, 2000, 3 pages.
cnn.com, "Paging Dr.Robot: Machine Helps Doctors with Patients", Sep. 30, 2003, 3 pages.
Crowley, Susan L., "Hello to Our Future", AARP Bulletin, Jan. 2000, 12 pages.
Dalton, Barnaby, "Techniques for Web Telerobotics", PhD Thesis, University of Western Australia, 2001, 243 pages.

Dario et al., "A Robot Workstation for Diagnosis and Physical Therapy", IEEE Catalog No. 88TH0234-5, 1989, pp. 67-72.
Davies, Brian, "Robotics in Minimally Invasive Surgery", IEE Colloquium on Through the Keyhole: Microengineering in Minimally Invasive Surgery, 1995, pp. 1-2.
Davis, Erik, "Telefriend, Meet iRobot, The Smartest Webcam on Wheels", Wired Magazine, Issue 8.09, Available onine at <http://www.wired.com/wired/archive/8.09/irobot.html?pg=1&topic=&topic_set=>, Sep. 2000, 3 pages.
Dean et al., "1992 AAAI Robot Exhibition and Competition", Articles, AI Magazine, vol. 14, No. 1, 1993, 15 pages.
Digiorgio, James, "Is Your Emergency Department of the 'Leading Edge?", Chicago Hospital News, vol. 2, No. 12, 2005, 3 pages.
Dudenhoeffer et al., "Command and Control Architectures for Autonomous Micro-Robotic Forces", FY00 Project Report, Idaho National Engineering and Environmental Laboratory Human Systems Engineering and Sciences Department, Idaho Falls, Apr. 2001, 43 pages.
Elhajj et al., "Real-Time Haptic Feedback in Internet-Based Telerobotic Operation", IEEE International Conference on Electro/Information Technology, available online at <http://www.egr.msu.edu/~ralab-web/cgi_bin/internet-teleoperation.php>, Jun. 2000, 10 pages.
Elhajj et al., "Supermedia in Internet-Based Telerobotic Operations", Management of Multimedia on the InternetLecture Notes in Computer Science, Springer-Verlag Berlin Heidelberg, vol. 2216, Oct. 29-Nov. 1, 2001, pp. 359-372.
Elhajj et al., "Synchronization and Control of Supermedia Transmission Via the Internet", Proceedings of 2001 International Symposium on Intelligent Multimedia Video and Speech Processing, May 2-4, 2001, pp. 320-323.
Ellison et al., "Telerounding and Patient Satisfaction Following Surgery", vol. 199, No. 4, Oct. 2004, pp. 523-530.
Evans et al., "The Trackless Robotic Courier", PYXIS HelpMate®, 2007, 3 pages.
Fels et al., "Developing a Video-Mediated Communication System for Hospitalized Children", Telemedicine Journal, vol. 5, No. 2, 1999, 30 pages.
Fetterman et al., "Videoconferencing Over the Internet", 2001, 8 pages.
Fiorini et al., "Health Care Robotics: A Progress Report", IEEE International Conference on Robotics and Automation, Apr. 20-25, 1997, pp. 1271-1276.
Fong, Terrence, "Collaborative Control: A Robot-Centric Model for Vehicle Teleoperation", Doctoral Dissertation, Technical Report CMU-RI-TR-01-34, Robotics Institute, Carnegie Mellon University, Nov. 2001, 197 pages.
Fulbright et al., "SWAMI: An Autonomous Mobile Robot for Inspection of Nuclear Waste of Storage Facilities", Autonomous Robots, vol. 2, 1995, pp. 225-235.
Gaidioz et al., "Synchronizing Network Probes to Avoid Measurement Intrusiveness with the Network Weather Service", Proceedings of the Ninth International Symposium on High-Performance Distributed Computing, 2000, pp. 147-154.
Garner et al., "The Application of Telepresence in Medicine", BT Technology Journal, vol. 15, No. 4, Oct. 1, 1997, pp. 181-187.
Ghiasi et al., "A Generic Web-based Teleoperations Architecture: Details and Experience", Proceedings of SPIE, Telemanipulator and Telepresence Technologies VI, vol. 3840, No. 234, Sep. 19, 1999, 14 pages.
Goldberg et al., "Collaborative Teleoperation via the Internet", IEEE International Conference on Robotics and Automation (ICRA), vol. 2, 2000, pp. 2019-2024.
Goldberg et al., "Desktop Teleoperation via the World Wide Web", IEEE International Conference on Robotics and Automation, vol. 1, May 21-27, 1995, pp. 654-659.
Goldenberg et al., "Telemedicine in Otolaryngology", American Journal of Otolaryngology, vol. 23,No. 1, 2002, pp. 35-43.
Goldman, Lea, "Machine Dreams", available online at <http://www.forbes.com/global/2002/0527/043.html>, May 27, 2002, 5 pages.

(56) References Cited

OTHER PUBLICATIONS

Gostai, "Gostai Jazz: Robotic Telepresence", available online at <http://www.robotshop.com/media/files/pdf/gostai-jazz-information-sheet.pdf>, 4 pages.
Gump, Michael D., "Robot Technology Improves VA Pharmacies", U.S. Medicine Informational Central, Jul. 2001, 3 pages.
Al-Kassab et al., "A Review of Telemedicine", Journal of Telemedicine and Telecare, vol. 5, Supplement 1, 1999, pp. 103-106.
Han et al., "Construction of an Omnidirectional Mobile Robot Platform Based on Active Dual-Wheel Caster Mechanisms and Development of a Control Simulator", Journal of Intelligent and Robotic Systems, vol. 29, Issue 3, Nov. 2000, pp. 257-275.
Handley et al., "RFC 2327—SDP: Session Description Protocol", available online at <http://www.faqs.org/rfcs/rfc2327.html>, Apr. 1998, 22 pages.
Hanebeck et al., "Roman: A Mobile Robotic Assistant for Indoor Service Applications", IEEE/RSJ International Conference on Intelligent Robots and Systems, vol. 2, Sep. 7-11, 1997, pp. 518-525.
Harmo et al., "Moving Eye-Interactive Telepresence Over Internet With a Ball Shaped Mobile Robot", available online at <http://automation.tkk.fi/files/tervetaas/MovingEye4.pdf>, 2000, 6 pages.
Haule et al., "Control Scheme for Delayed Teleoperation Tasks", IEEE Pacific Rim Conference on Communications, Computers, and Signal Processing, May 17-19, 1995, pp. 157-160.
Hees, William P., "Communications Design for a Remote Presence Robot", CSCI E-131b, Final Project, Jan. 14, 2002, 12 pages.
Herias et al., "Flexible Virtual and Remote Laboratory for Teaching Robotics", Current Developments in Technology-Assisted Education, Jun. 2006, pp. 1959-1963.
Holmberg et al., "Development of a Holonomic Mobile Robot for Mobile Manipulation Tasks", International Journal of Robotics Research, vol. 19, No. 11, Nov. 2000, pp. 1066-1074.
Ishiguro et al., "Integrating a Perceptual Information Infrastructure with Robotic Avatars: A Framework for Tele-Existence", IEEE/RSJ International Conference on Intelligent Robots and Systems, vol. 2, 1999, pp. 1032-1038.
Ishihara et al., "Intelligent Microrobot DDS (Drug Delivery System) Measured and Controlled by Ultrasonics", Intelligent Robots and Systems '91. Intelligence for Mechanical Systems, IEEE/RSJ International Workshop, vol. 2, Nov. 3-5, 1991, pp. 1145-1150.
ITU, "Call Completion Supplementary Services for H.323", ITU-T, Telecommunication Standardization Sector of ITU, H.450.9, Series H: Audiovisual and Multimedia Systems, Nov. 2000, 63 pages.
ITU, "Call Intrusion Supplementary Service for H.323", ITU-T, Telecommunication Standardization Sector of ITU, H.450.11, Series H: Audiovisual and Multimedia Systems, Mar. 2001, 59 pages.
ITU, "Packet-Based Multimedia Communications Systems", ITU-T, Telecommunication Standardization Sector of ITU, H.323, Series H: Audiovisual and Multimedia Systems, Feb. 1998, 128 pages.
ITU, "Transmission of Non-Telephone Signals: A Far End Camera Control Protocol for Videoconferences Using H.224", ITU-T, Telecommunication Standardization Sector of ITU, H.281, Nov. 1994, 12 pages.
Paulos, Eric John, "Personal Tele-Embodiment", OskiCat Catalog Record, UCB Library Catalog, 2001, 3 pages.
Paulos et al., "Personal Tele-Embodiment", Chapter 9 in Goldberg, et al., ed. "Beyond webcams", MIT Press, Jan. 4, 2002, pp. 155-167.
Paulos, Eric John, "Personal Tele-Embodiment", Introductory and cover pages from 2001 Dissertation including Contents table, together with e-mails relating thereto from UC Berkeley Libraries, as shelved at UC Berkeley Engineering Library (Northern Regional library Facility), May 8, 2002, 25 pages (including 4 pages of e-mails).
Paulos et al., "PRoP: Personal Roving Presence", ACM:CHI Proceedings of CHI '98, 1998, 8 pages.
Paulos et al., "Social Tele-Embodiment: Understanding Presence", Autonomous Robots, vol. 11, Issue 1, Kluwer Academic Publishers, Jul. 2001, pp. 87-95.
Paulos et al., "Ubiquitous Tele-Embodiment: Applications and Implications", International Journal of Human Computer Studies, vol. 46, No. 6, Jun. 1997, pp. 861-877.
Paulos, Eric John Canny, "Video of PRoP 2 at Richmond Field Station", www.prop.org Printout of Home Page of Website and two-page Transcript of the audio portion of said PRoP Video, May 2001, 2 pages.
PictureTel Corporation, "PictureTel Live200 for Windows NT Product Guide", 1997, 63 pages.
Pin et al., "A New Family of Omnidirectional and Holonomic Wheeled Platforms for Mobile Robots", IEEE Transactions on Robotics and Automation, vol. 10, No. 4, Aug. 1994, pp. 480-489.
Piquepaille, Roland, "This Blog and its RSS Feed Are Moving", Roland Piquepaille's Technology Trends, How new technologies are modifying our way of life, Oct. 31, 2004, 2 pages.
West et al., "Design of Ball Wheel Mechanisms for Omnidirectional Vehicles with Full Mobility and Invariant Kinematics", Journal of Mechanical Design, vol. 119, Jun. 1997, pp. 153-161.
Yamasaki et al., "Applying Personal Robots and Active Interface to Video Conference Systems", 6th International Conference on Human Computer Interaction, vol. B, 1995, pp. 243-248.
Yamauchi, Brian, "PackBot: A Versatile Platform for Military Robotics", Proceedings of SPIE for Military Robotics, 2004, pp. 228-237.
Yong et al., "Robot Task Execution with Telepresence Using Virtual Reality Technology", 1998 International Conference on Mechatronic Technology, Nov. 30-Dec. 2, 1998, pp. 1-8.
Zambroski, James, "CMU, Pitt Developing 'Nursebot'", available online at <http://www.cs.cmu.edu/~nursebot/web/press/tribunereview.html>, Oct. 27, 2000, 3 pages.
Radvision, "Making Sense of Bandwidth the Netsense Way", Network Congestion in Unmanaged Networks Bandwidth Estimation and Adaptation Techniques, White Paper, Radvision's Netsense Technology, 2010, 7 pages.
Reynolds et al., "Review of Robotic Telemedicine Utilization in Intensive Care Units (ICUs)", 11th Annual ATA Symposium, Tampa, Florida, 2011, 1 page.
Roach, Adam, "Automatic Call Back Service in SIP", Internet Engineering Task Force, Internet Draft, Category: Informational, Mar. 2000, 8 pages.
Rovetta et al., "A New Telerobotic Application: Remote Laparoscopic Surgery Using Satellites and optical fiber Networks for Data Exchange", International Journal of Robotics Research, vol. 15, No. 3, Jun. 1, 1996, pp. 267-279.
Roy et al., "Towards Personal Service Robots for the Elderly", Workshop on Interactive Robots and Entertainment (Wire 2000), available online at <http://www.ri.cmu.edu/pb_files/pub2/roy_nicholas_2000_1/roy_nicholas_2000_1.pdf>, vol. 25, Apr. 30-May 1, 2000, 7 pages.
Sachs et al., "Virtual Visit: Improving Communication for Those Who Need it Most", Studies in Health Technology and Informatics, vol. 94, Medicine Meets Virtual Reality 11, 2003, pp. 302-308.
Salemi et al., "MILO: Personal Robot Platform", IEEE/RSJ International Conference on Intelligent Robots and Systems, Aug. 2005, pp. 4089-4094.
Sandt et al., "Perceptions for a Transport Robot in Public Environments", Proceedings of the 1997 IEEE/RSJ International Conference on Intelligent Robots and Systems, vol. 1, Sep. 7-11, 1997, pp. 360-365.
Sawyer, Robert J., "Inventing the Future: 2000 Years of Discovery", available online at <http://www.sfwriter.com/pritf.htm>, Jan. 2, 2000, 2 pages.
Schaeffer et al., "Care-O-BotTM: The Concept of a System for Assisting Elderly or Disabled Persons in Home Environments", Proceedings of the 24th Annual Conference of the IEEE Industrial Electronics Society, vol. 4, 1998, pp. 2476-2481.
Schraft et al., "Care-O-bot™: The Concept of a System for Assisting Elderly or Disabled Persons in Home Environments", IEEE Proceedings of the 24th Annual Conference of the Industrial Electronics Society, IECON '98, Aug. 31-Sep. 4, 1998, pp. 2476-2481.
Schultz et al., "Web Interfaces for Mobile Robots in Public Places", IEEE Robotics & Automation Magazine, vol. 7, No. 1, Mar. 2000, pp. 48-56.

(56) References Cited

OTHER PUBLICATIONS

Shimoga et al., "Touch and Force Reflection for Telepresence Surgery", Proceedings of the 16th Annual International Conference of the IEEE Engineering in Medicine and Biology Society, Nov. 1994, pp. 1049-1050.

Siegwart et al., "Interacting Mobile Robots on the Web", Proceedings of the 1999 IEEE International Conference on Robotics and Automation, May 1999, pp. 1-7.

Simmons et al., "Xavier: An Autonomous Mobile Robot on the Web", IEEE Robotics and Automation Magazine, 1999, pp. 43-48.

Stephenson, Gary, "Dr. Robot Tested at Hopkins", available online at <http://www.hopkinsmedicine.org/press/2003/august/030805.htm>, Aug. 5, 2003, 2 pages.

Stoianovici et al., "Robotic Tools for Minimally Invasive Urologic Surgery", Complications of Urologic Laparoscopic Surgery: Recognition, Management and Prevention, Dec. 2002, 17 pages.

Suplee, Curt, "Mastering the Robot", The Washington Post, Washington Post Staff Writer, Sep. 17, 2000, 5 pages.

Tahboub et al., "Dynamics Analysis and Control of a Holonomic Vehicle With Continuously Variable Transmission", Transactions of the ASME, Journal of Dynamic Systems, Measurement and Control, vol. 124, Mar. 2002, pp. 118-126.

Telepresence Research, Inc., "The Telepresence Mobile Robot System", available online at <http://www.telepresence.com/telepresence-research/TELEROBOT/>, Feb. 20, 1995, 3 pages.

Tendick et al., "Human-Machine Interfaces for Minimally Invasive Surgery", Proceedings of the 19th Annual International Conference of the IEEE Engineering in Medicine and Biology Society, vol. 6, Oct. 30-Nov. 2, 1997, pp. 2771-2776.

Theodosiou et al., "MuLVAT: A Video Annotation Tool Based on XML-Dictionaries and Shot Clustering", 19th International Conference, Artificial Neural Networks—ICANN 2009, Part II, Sep. 14-17, 2009, pp. 913-922.

Thrun et al., "Probabilistic Algorithms and the Interactive Museum Tour-Guide Robot Minerva", International Journal of Robotics Research, vol. 19, 2000, pp. 1-35.

Time, Lists, "Office Coworker Robot", Best Inventions of 2001, available online at <http://content.time.com/time/specials/packages/article/0,28804,1936165_1936255_1936640,00.html>, Nov. 19, 2001, 2 pages.

Tipsuwan et al., "Gain Adaptation of Networked Mobile Robot to Compensate QoS Deterioration", 28th Annual Conference of the Industrial Electronics Society, vol. 4, Nov. 5-8, 2002, pp. 3146-3151.

Tsui et al., "Exploring Use Cases for Telepresence Robots", 6th ACM/IEEE International Conference on Human-Robot Interaction (HRI), Mar. 2011, pp. 11-18.

Tyrrell et al., "Teleconsultation in Psychology: The Use of Videolinks for Interviewing and Assessing Elderly Patients", Age and Ageing, vol. 30, No. 3, May 2001, pp. 191-195.

Tzafestas et al., "VR-Based Teleoperation of a Mobile Robotic Assistant: Progress Report", Technical Report DEMO 2000/13, Institute of Informatics and Telecommunications, National Center for Scientific Research "Demokritos", Nov. 2000, pp. 1-23.

UMASS Lowell Robotics Lab, "Robotics Lab @ UMASS Lowell", Brochure, 2011, 2 pages.

Urquhart, Kim, "InTouch's Robotic Companion 'Beams Up' Healthcare Experts", Medical Device Daily, vol. 7, No. 39, Feb. 27, 2003, pp. 1, 4.

Video Middleware Cookbook, "H.350 Directory Services for Multimedia", 2 pages.

Weaver et al., "Monitoring and Controlling Using the Internet and Java", Proceedings of the 25th Annual Conference of the IEEE Industrial Electronics Society, vol. 3, 1999, pp. 1152-1158.

Weiss et al., "Pebbles: A Personal Technology for Meeting Education, Social and Emotional Needs of Hospitalised Children", Personal and Ubiquitous Computing, vol. 5, No. 3, Aug. 2001, pp. 157-168.

Jouppi et al., "BiReality: Mutually-Immersive Telepresence", Proceedings of the 12th Annual ACM International Conference on Multimedia, Oct. 10-16, 2004, pp. 860-867.

Jouppi et al., "First Steps Towards Mutually-Immersive Mobile Telepresence", Proceedings of the 2002 ACM Conference on Computer Supported Cooperative Work, Nov. 16-20, 2002, pp. 354-363.

Kanehiro et al., "Virtual Humanoid Robot Platform to Develop Controllers of Real Humanoid Robots without Sorting", IEEE/RSJ International Conference on Intelligent Robots and Systems, vol. 2, 2001, pp. 1093-1099.

Kaplan et al., "An Internet Accessible Telepresence", Multimedia Systems Journal, vol. 5, 1996, 7 pages.

Keller et al., "Raven Interface Project", The National Aviary's Teleconferencing Carnegie Mellon University Robot, Interaction and Visual Interface Design, School of Design, Carnegie Mellon University, 2001, 8 pages.

Khatib et al., "Robots in Human Environments", Proceedings International Conference on Control, Automation, Robotics, and Vision ICRACV2000, 1999, 15 pages.

Knight et al., "Active Visual Alignment of a Mobile Stereo Camera Platform", IEEE International Conference on Robotics and Automation, vol. 4, Apr. 24-28, 2000, pp. 3203-3208.

Koenen, Rob, "MPEG-4: a Powerful Standard for Use in Web and Television Environments", (KPN Research), available online at <http://www.w3.org/Architecture/1998/06/Workshop/paper26>, Jul. 1, 1998, 4 pages.

Kurlowicz et al., "The Mini Mental State Examination (MMSE)", Try This: Best Practices in Nursing Care to Older Adults, A series from the Hartford Institute of Geriatric Nursing, Issue No. 3, Jan. 1999, 2 pages.

Kuzuoka et al., "Can the GestureCam Be a Surrogate?", Proceedings of the Fourth European Conference on Computer-Supported Cooperative Work, 1995, pp. 181-196.

Lane, Earl, "Automated Aides", Available online at <http://www.cs.cum.edu/nursebot/web/press/nd4380.htm>, Oct. 17, 2000, 4 pages.

Lee et al., "A Novel Method of Surgical Instruction: International Telementoring", World Journal of Urology, vol. 16, No. 6, Dec. 1998, pp. 367-370.

Leifer et al., "VIPRR: A Virtually in Person Rehabilitation Robot", Proceedings of 1997 International Conference on Rehabilitation Robotics, Apr. 14-15, 1997, 4 pages.

Lemaire, Edward, "Using Communication Technology to Enhance Rehabilitation Services: A Solution Oriented User Manual", Institute for Rehabilitation Research and Development, Terry Fox Mobile Clinic, The Rehabilitation Centre, Ottawa, Ontario, Canada, Version 2.0, available online at <http://www.ird.ca/telehealth/distfile/distman_v2_1.pdf>, 1998-2001, 104 pages.

Library of Congress, "008-Fixed-Length Data Elements (NR)", MARC 21 Format for Classification Data, available online at <http://www.loc.gov/marc/classification/cd008.html>, Jan. 2000, pp. 1-14.

Lim et al., "Control to Realize Human-Like Walking of a Biped Humanoid Robot", IEEE International Conference on Systems, Man, and Cybernetics, 2000, vol. 5, 2000, pp. 3271-3276.

Linebarger et al., "Concurrency Control Mechanisms for Closely Coupled Collaboration in Multithreaded Virtual Environments", Department of Computer Science and Engineering, Lehigh University, vol 13, 2004, 40 pages.

Long, William F., "Robot Navigation Technology", available online at <http://www.atp.nist.gov/eao/sp950-1/helpmate.htm>, Mar. 1999, 3 pages.

Luna, Nancy, "Robot a New Face on Geriatric Care", ocregister.com, Aug. 6, 2003, 3 pages.

Mack, Michael J., "Minimally Invasive and Robotic Surgery", The Journal of the American Medical Association, vol. 285, No. 5, 2001, pp. 568-572.

Mair, G. M., "Telepresence—The Technology and its Economic and Social Implications", Technology and Society, 1997. 'Technology and Society at a Time of Sweeping Change'. Proceedings, 1997 International Symposium, Jun. 20-21, 1997, pp. 118-124.

Martin, Anya, "Brighter Days Ahead", Assisted Living Today, vol. 9, Nov./Dec. 2002, pp. 19-22.

(56) References Cited

OTHER PUBLICATIONS

McCardle et al., "The Challenge of Utilizing New Technology in Design Education", Loughborough University, IDATER 2000, 2000, pp. 122-127.

Meng et al., "E-Service Robot in Home Healthcare", Proceedings of the 2000 IEEE/RSJ, International Conference on Intelligent Robots and Systems, 2000, pp. 832-837.

Metz, Cade, "HP Labs", available online at <http://www.pcmag.com/article2/0,2817,1130820,00.asp>, Jul. 1, 2003, 4 pages.

Michaud, Anne, "Introducing "Nursebot"", available online at <http://www.cs.cmu.edu/nursebot/web/press/globe 301/index.html>, 2001, 4 pages.

Microsoft Corporation, Inc., "Microsoft NetMeeting 3 Features excerpt from Official Microsoft NetMeeting 3.0 Book", available online at <http://technet.microsoft.com/en-us/library/cc723477.aspx>, 2012, 6 pages.

Minsky, Marvin, "Telepresence", OMNI Magazine, Jun. 1980, 6 pages.

Montemerlo, Reddy Whittaker, "Telepresence: Experiments in Next Generation Internet", available online at <http://www.ri.cmu.edu/creative/archives.htm>, Oct. 20, 1998, 3 pages.

Murphy, Robin R., "Introduction to AI Robotics", A Bradford Book, The MIT Press, Cambridge, Massachusetts, London, England, 2000, 487 pages.

Nakajima et al., "A Multimedia Teleteaching System using an Electronic Whiteboard for Two Way Communication of Motion Videos and Chalkboards", 2nd IEEE International Workshop on Robot and Human Communication, 1993, pp. 436-441.

Nakazato et al., "Group-Based Interface for Content-Based Image Retrieval", Proceedings of the Working Conference on Advanced Visual Interfaces, 2002, pp. 187-194.

Nakazato et al., "ImageGrouper: A Group-Oriented User Interface for Content-Based Image Retrieval and Digital Image Arrangement", Journal of Visual Languages & Computing, vol. 14, No. 4, Aug. 2003, pp. 45-46.

Nersc, "Berkeley Lab's RAGE Telepresence Robot Captures R&D100 Award", Available online at <https://www.nersc.gov/news-publications/news/nersc-center-news/2002/berkeley-lab-s-rage-telepresence-robot-captures-r-and-d100-award/>, Jul. 2, 2002, 2 pages.

Nomadic Technologies Inc., "Nomad XR4000 Hardware Manual", Release 1.0, Mar. 1999, 34 pages.

Noritsugu et al., "Application of Rubber Artificial Muscle Manipulator as a Rehabilitation Robot", Mechatronics, IEEE/ASME Transactions, vol. 2, No. 4, Dec. 1997, pp. 259-267.

North, Michael, "Telemedicine: Sample Script and Specifications for a Demonstration of Simple Medical Diagnosis and Treatment Using Live Two-Way Video on a Computer Network", Greenstar Corporation, 1998, 5 pages.

Ogata et al., "Development of Emotional Communication Robot: WAMOEBA-2R—Experimental Evaluation", Proceedings of the 2000 IEEE/RSJ International Conference on Intelligent Robots and Systems, vol. 1, 2000, pp. 175-180.

Ogata et al., "Emotional Communication Robot: WAMOEBA-2R—Emotion Model and Evaluation Experiments", Proceedings of the International Conference on Humanoid Robots, 2000, pp. 1-16.

Oh et al., "Autonomous Battery Recharging for Indoor Mobile Robots", Proceedings of Australian Conference on Robotics and Automation, 2000, pp. 1-6.

Ojha, Anand K., "An application of Virtual Reality in Rehabilitation", Proceedings of the 1994 IEEE Southeastcon 94. Creative Technology Transfer—A Global Affair, Apr. 1994, pp. 4-6.

Osborn, Jim, "Quality of Life Technology Center", QoLT Research Overview: A National Science Foundation Engineering Research Center, Carnegie Mellon University of Pittsburgh, 2 pages.

Panusopone et al., "Performance comparison of MPEG-4 and H.263+ for streaming video applications", Circuits Systems Signal Processing, vol. 20, No. 3, 2001, pp. 293-309.

Paulos et al., "A World Wide Web Telerobotic Remote Environment Browser", Available online at <http://www.w3.org/Conferences/WWW4/Papers/326/>, 1995, 15 pages.

Paulos et al., "Designing Personal Tele-Embodiment", Proceedings of IEEE International Conference on Robotics and Automation, vol. 4, May 16-20, 1998, pp. 3173-3178.

Paulos, Eric J., "Personal Tele-Embodiment", Dissertation, Doctor of Philosophy in Computer Science in the Graduate Division of the University of California at Berkeley, 2001, 282 pages.

Weiss et al., "Telework and Video-Mediated Communication: Importance of Real-Time, Interactive Communication for Workers with Disabilities", available online at <http://www.telbotics.com/research_3.htm>, retrieved on Nov. 23, 2010, 3 pages.

Zamrazil, Kristie, "Telemedicine in Texas: Public Policy Concerns", Focus Report, House Research Organization, Texas House of Representatives, No. 76-22, May 5, 2000, pp. 1-16.

Zipperer, Lorri, "Robotic Dispensing System", ISMP Medication Safety Alert!, vol. 4, No. 17, Aug. 25, 1999, 2 pages.

Zorn, Benjamin G., "Ubiquitous Telepresence", Department of Computer Science, University of Colorado, 1996, 13 pages.

\* cited by examiner

PROTOCOL FOR A REMOTELY CONTROLLED VIDEOCONFERENCING ROBOT

BACKGROUND OF THE INVENTION

1. Field of the Invention

The subject matter disclosed generally relates to the field of robotics.

2. Background Information

There is a growing need to provide remote health care to patients that have a variety of ailments ranging from Alzheimers to stress disorders. To minimize costs it is desirable to provide home care for such patients. Home care typically requires a periodic visit by a health care provider such as a nurse or some type of assistant. Due to financial and/or staffing issues the health care provider may not be there when the patient needs some type of assistance. Additionally, existing staff must be continuously trained, which can create a burden on training personnel. It would be desirable to provide a system that would allow a health care provider to remotely care for a patient without being physically present.

Robots have been used in a variety of applications ranging from remote control of hazardous material to assisting in the performance of surgery. For example, U.S. Pat. No. 5,762,458 issued to Wang et al. discloses a system that allows a surgeon to perform minimally invasive medical procedures through the use of robotically controlled instruments. One of the robotic arms in the Wang system moves an endoscope which has a camera that allows a surgeon to view a surgical area of a patient.

Tele-robots such as hazardous waste handlers and bomb detectors may contain a camera that allows the operator to view the remote site. Canadian Pat. No. 2289697 issued to Treviranus, et al. discloses a teleconferencing platform that has both a camera and a monitor. The Treviranus patent also discloses embodiments with a mobile platform, and different mechanisms for moving the camera and the monitor.

Publication Application No. US-2003-0050233-A1 discloses a remote robotic system wherein a plurality of remote stations can control a plurality of robotic arms used to perform a minimally invasive medical procedure. Each remote station can receive a video image provided by the endoscope inserted into the patient. The remote stations are linked to the robotic system by a dedicated communication link. The dedicated link is required to insure communication quality during the performance of remote surgical procedure. Dedicated links are not practical for a robotic product that can be used by a number of operators.

BRIEF SUMMARY OF THE INVENTION

A robotic system that includes a robot and a remote station that communicate through a broadband network. Control commands can be sent from the remote station to the robot through the broadband network. Reporting commands can be sent to the remote station from the robot.

DETAILED DESCRIPTION

Disclosed is a robotic system that includes a robot and a remote station. The remote station can generate control commands that are transmitted to the robot through a broadband network. The control commands can be interpreted by the robot to induce action such as robot movement or focusing a robot camera. The robot can generate reporting commands that are transmitted to the remote station through the broadband network. The reporting commands can provide positional feedback or system reports on the robot.

Figure 1:
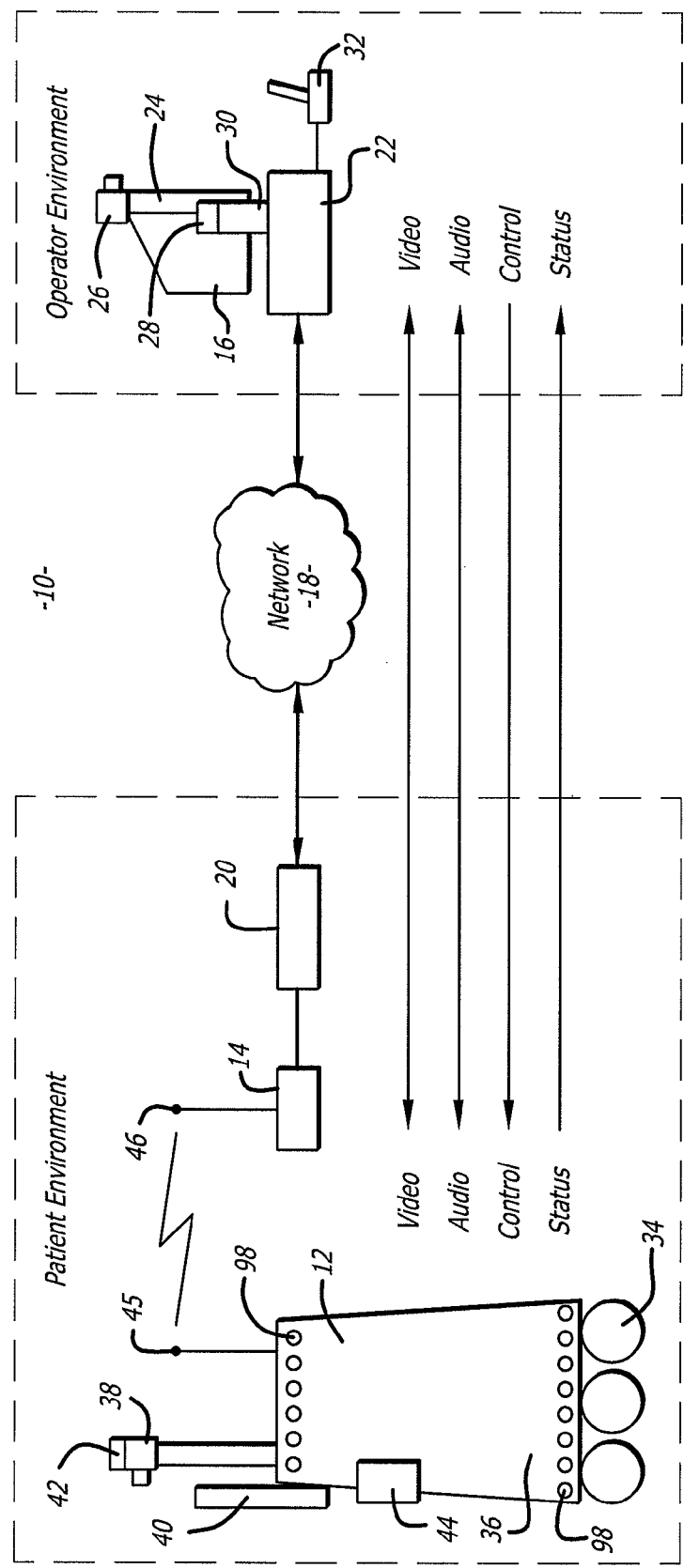
FIG. 1 is an illustration of a robotic system.

Referring to the drawings more particularly by reference numbers, FIG. 1 shows a robotic system 10. The robotic system 10 includes a robot 12, a base station 14 and a remote control station 16. The remote control station 16 may be coupled to the base station 14 through a network 18. By way of example, the network 18 may be either a packet switched network such as the Internet, or a circuit switched network such has a Public Switched Telephone Network (PSTN), or other broadband system. The base station 14 may be coupled to the network 18 by a modem 20 or other broadband network interface device.

The remote control station 16 may include a computer 22 that has a monitor 24, a camera 26, a microphone 28 and a speaker 30. The computer 22 may also contain an input device 32 such as a joystick or a mouse. The control station 16 is typically located in a place that is remote from the robot 12. Although only one robot 12 and one station 16 are shown, it is to be understood that the system 10 may have a plurality of robots 12 and/or a plurality of remote stations that communicate through the broadband network. In general any number of robots 12 may be controlled by any number of remote stations. For example, one remote station 16 may be coupled to a plurality of robots 12, or one robot 12 may be coupled to a plurality of remote stations 16.

The robot 12 includes a movement platform 34 that is attached to a robot housing 36. Also attached to the robot housing 36 are a camera 38, a monitor 40, a microphone(s) 42 and a speaker 44. The microphone 42 and speaker 30 may create a stereophonic sound. The robot 12 may also have an antenna 45 that is wirelessly coupled to an antenna 46 of the base station 14. The system 10 allows a user at the remote control station 16 to move the robot 12 through the input device 32. The robot camera 38 is coupled to the remote monitor 24 so that a user at the remote station 16 can view a patient. Likewise, the robot monitor 40 is coupled to the remote camera 26 so that the patient can view the user. The microphones 28 and 42, and speakers 30 and 44, allow for audible communication between the patient and the user.

Each remote station computer 22 may operate Microsoft OS software and WINDOWS XP or other operating systems such as LINUX. The remote computer 22 may also operate a video driver, a camera driver, an audio driver and a joystick driver. The video images may be transmitted and received with compression software such as MPEG CODEC.

Figure 2:
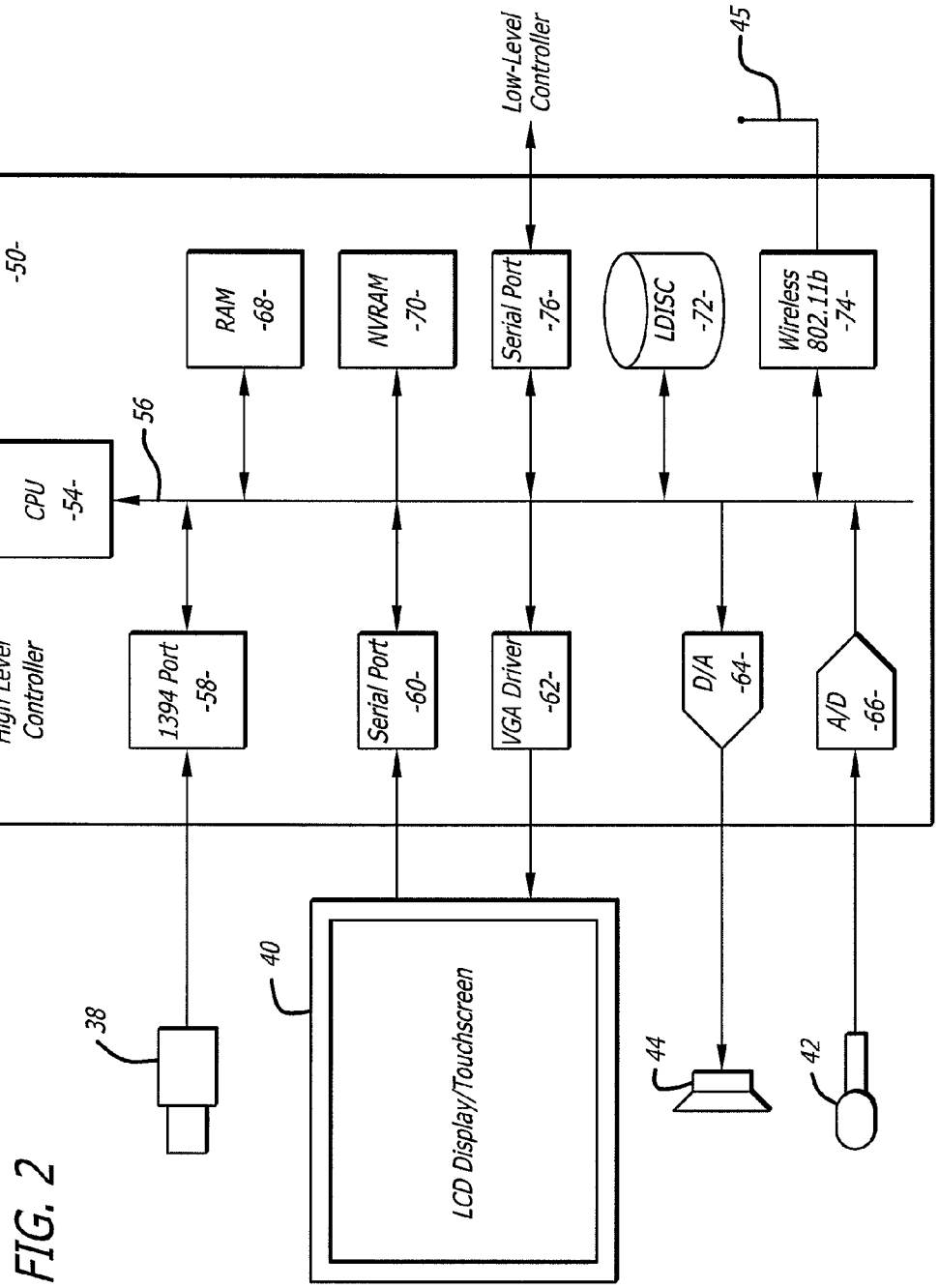
FIG. 2 is a schematic of an electrical system of a robot.
Figure 3:
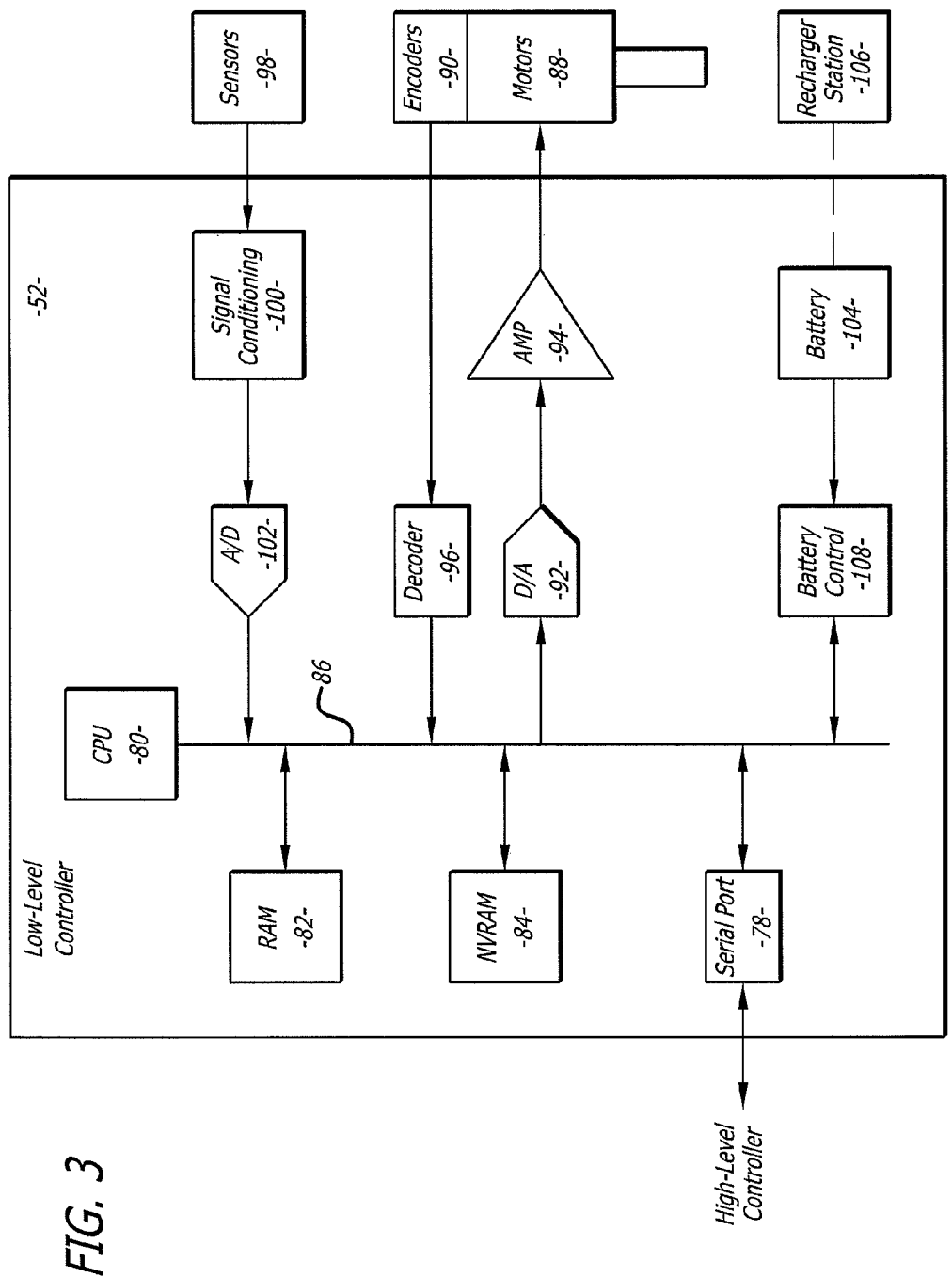
FIG. 3 is a further schematic of the electrical system of the robot.

FIGS. 2 and 3 show an embodiment of the robot 12. The robot 12 may include a high level control system 50 and a low level control system 52. The high level control system 50 may include a processor 54 that is connected to a bus 56. The bus is coupled to the camera 38 by an input/output (I/O) port 58, and to the monitor 40 by a serial output port 60 and a VGA driver 62. The monitor 40 may include a touchscreen function that allows the patient to enter input by touching the monitor screen.

The speaker 44 is coupled to the bus 56 by a digital to analog converter 64. The microphone 42 is coupled to the bus 56 by an analog to digital converter 66. The high level controller 50 may also contain random access memory (RAM) device 68, a non-volatile RAM device 70 and a mass storage device 72 that are all coupled to the bus 62. The mass storage device 72 may contain medical files of the patient that can be accessed by the user at the remote control station 16. For example, the mass storage device 72 may contain a picture of the patient. The user, particularly a health care provider, can recall the old picture and make a side by side comparison on the monitor 24 with a present video image of the patient provided by the camera 38. The robot antennae 45 may be coupled to a wireless transceiver 74. By way of example, the transceiver 74 may transmit and receive information in accordance with IEEE 802.11b.

The controller 54 may operate with a LINUX OS operating system. The controller 54 may also operate MS WINDOWS along with video, camera and audio drivers for communication with the remote control station 16. Video information may be transceived using MPEG CODEC compression techniques. The software may allow the user to send e-mail to the patient and vice versa, or allow the patient to access the Internet. In general the high level controller 50 operates to control the communication between the robot 12 and the remote control station 16.

The high level controller 50 may be linked to the low level controller 52 by serial ports 76 and 78. The low level controller 52 includes a processor 80 that is coupled to a RAM device 82 and non-volatile RAM device 84 by a bus 86. The robot 12 contains a plurality of motors 88 and motor encoders 90. The encoders 90 provide feedback information regarding the output of the motors 88. The motors 88 can be coupled to the bus 86 by a digital to analog converter 92 and a driver amplifier 94. The encoders 90 can be coupled to the bus 86 by a decoder 96. The robot 12 also has a number of proximity sensors 98 (see also FIG. 1). The position sensors 98 can be coupled to the bus 86 by a signal conditioning circuit 100 and an analog to digital converter 102.

The low level controller 52 runs software routines that mechanically actuate the robot 12. For example, the low level controller 52 provides instructions to actuate the movement platform to move the robot 12. The low level controller 52 may receive movement instructions from the high level controller 50. The movement instructions may be received as movement commands from the remote control station 16. Although two controllers are shown, it is to be understood that the robot 12 may have one controller controlling the high and low level functions.

The various electrical devices of the robot 12 may be powered by a battery(ies) 104. The battery 104 may be recharged by a battery recharger station 106 (see also FIG. 1). The low level controller 52 may include a battery control circuit 108 that senses the power level of the battery 104. The low level controller 52 can sense when the power falls below a threshold and then send a message to the high level controller 50. The high level controller 50 may include a power management software routine that causes the robot 12 to move so that the battery 104 is coupled to the recharger 106 when the battery power falls below a threshold value. Alternatively, the user can direct the robot 12 to the battery recharger 106. Additionally, the battery 104 may be replaced or the robot 12 may be coupled to a wall power outlet by an electrical cord (not shown).

Figure 4:
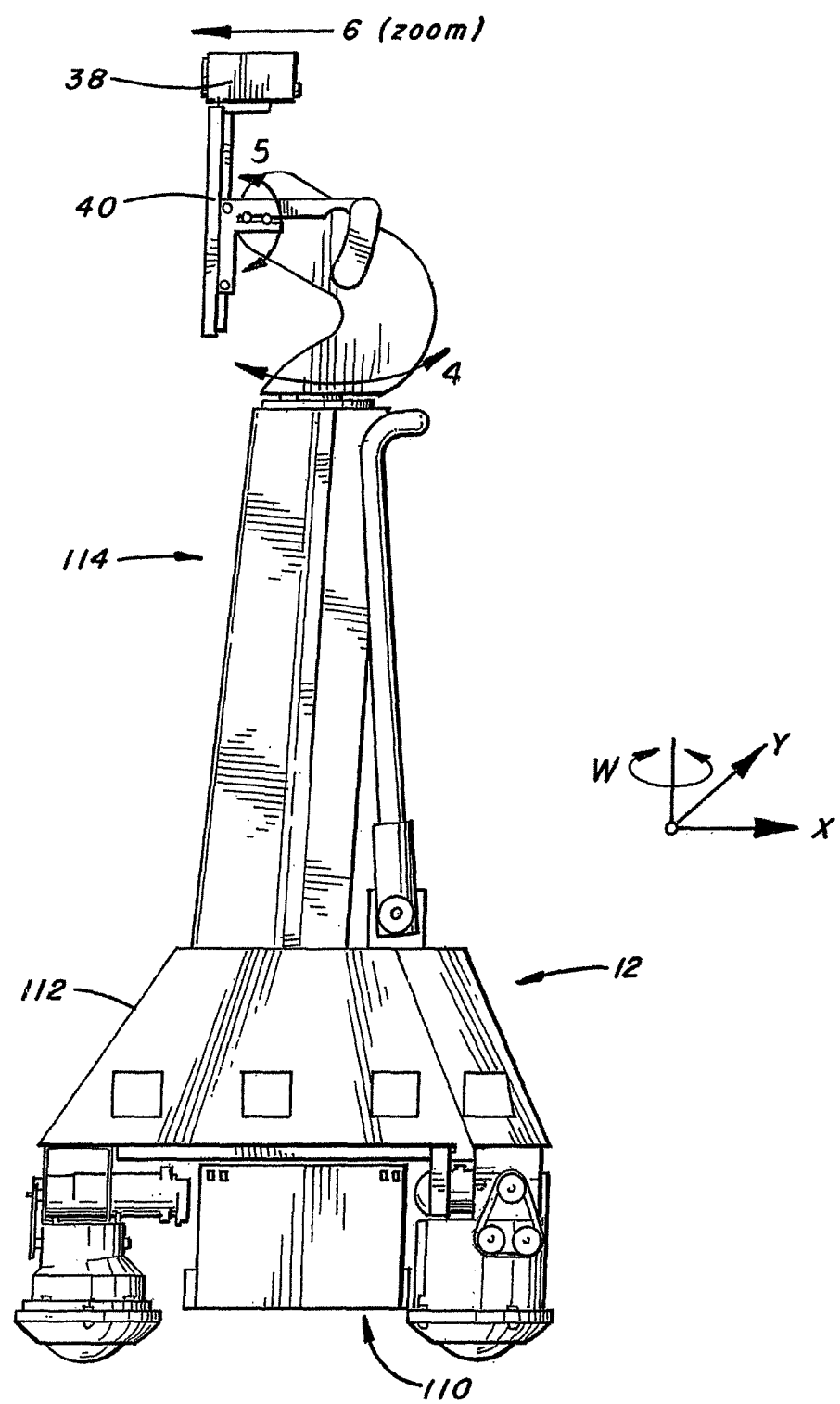
FIG. 4 is side view of the robot.

FIG. 4 shows an embodiment of the robot 12. The robot 12 may include a holonomic platform 110 that is attached to a robot housing 112. The holonomic platform 110 provides three degrees of freedom to allow the robot 12 to move in any direction.

The robot 12 may have an pedestal assembly 114 that supports the camera 38 and the monitor 40. The pedestal assembly 114 may have two degrees of freedom so that the camera 26 and monitor 24 can be swiveled and pivoted as indicated by the arrows.

Figure 5:
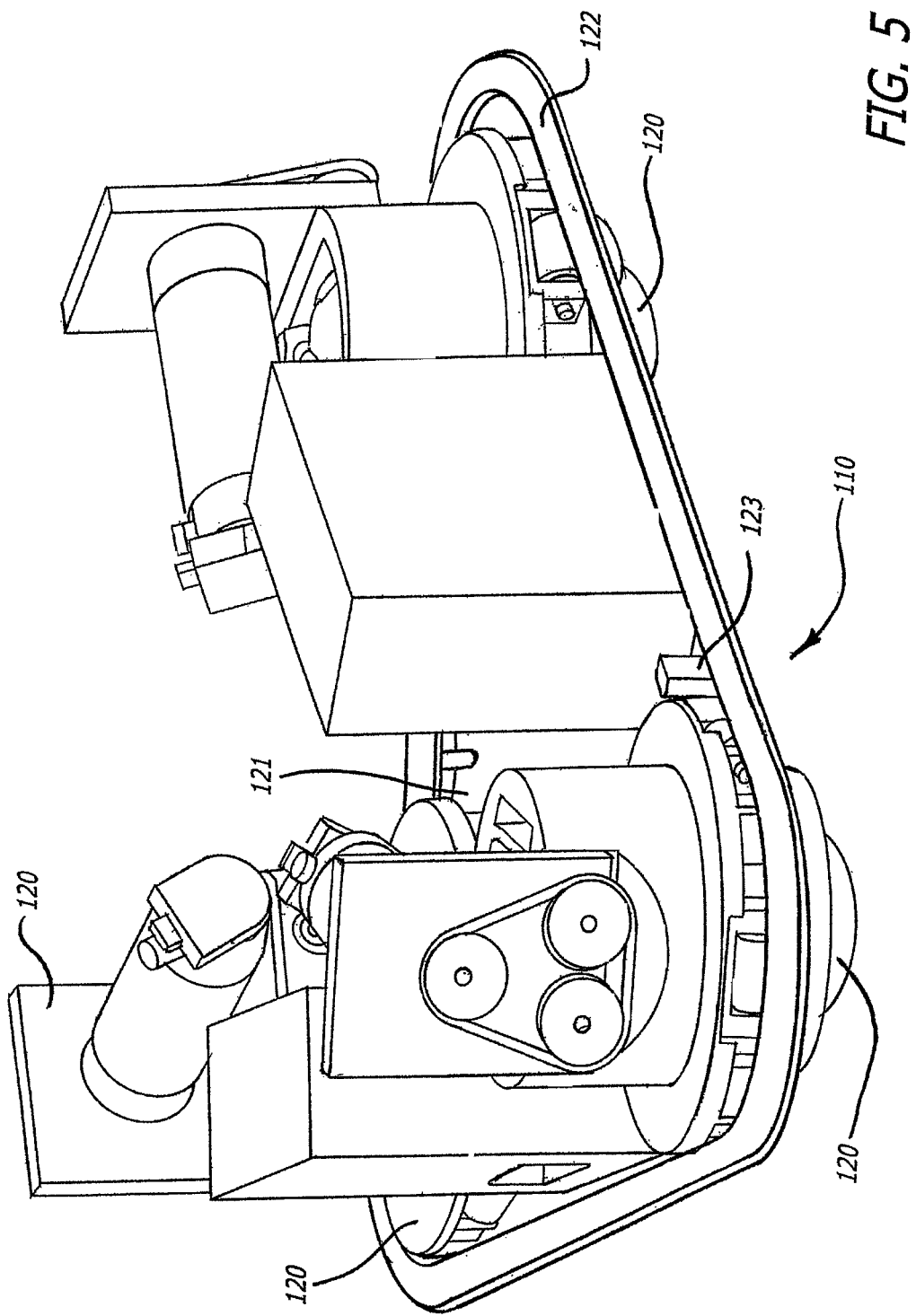
FIG. 5 is a top perspective view of a holonomic platform of the robot.

As shown in FIG. 5 the holonomic platform 110 may include three roller assemblies 120 that are mounted to a base plate 121. The roller assemblies 120 are typically equally spaced about the platform 110 and allow for movement in any direction, although it is to be understood that the assemblies may not be equally spaced.

The robot housing 112 may include a bumper 122. The bumper 122 may be coupled to optical position sensors 123 that detect when the bumper 122 has engaged an object. After engagement with the object the robot can determine the direction of contact and prevent further movement into the object.

Figure 6:
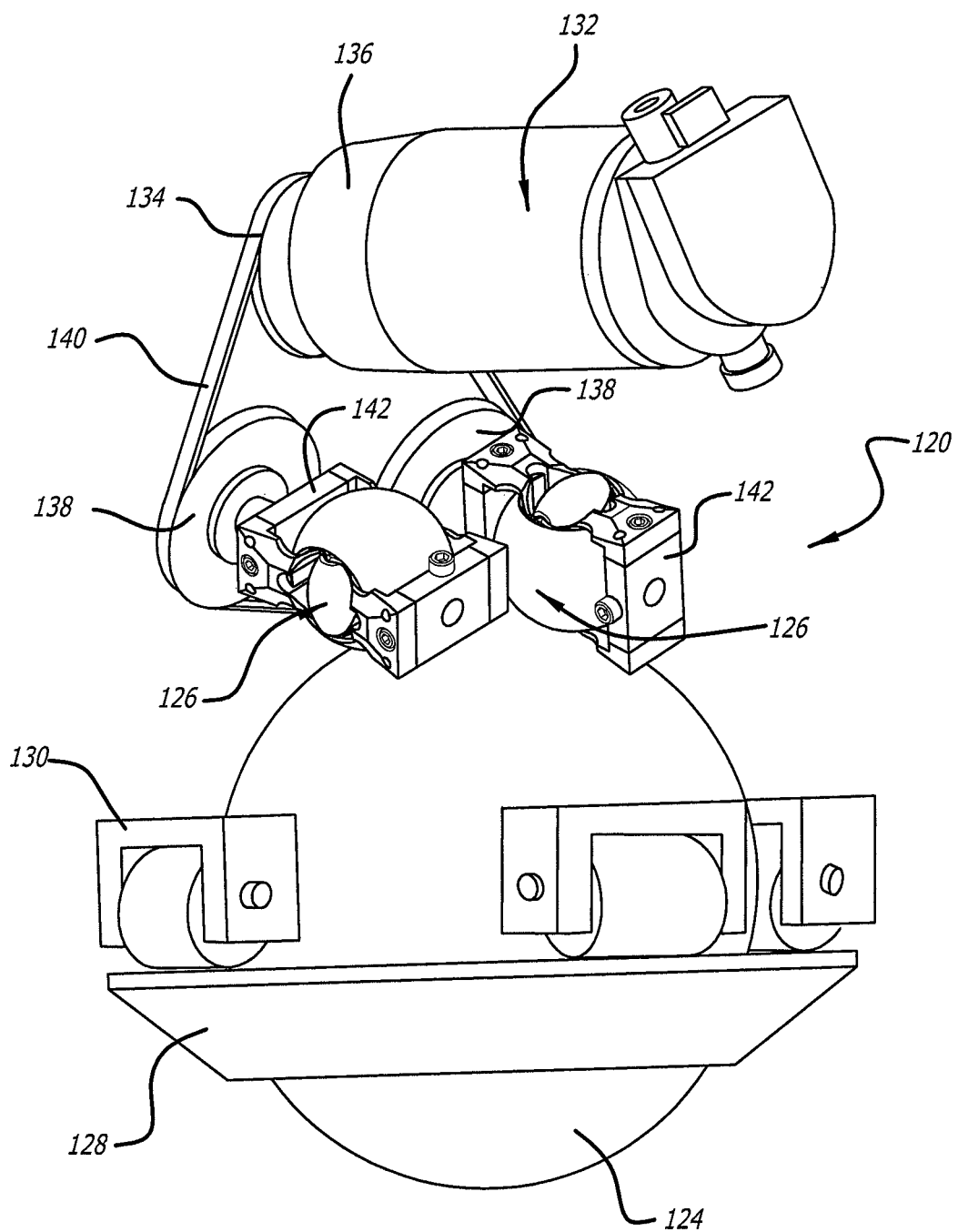
FIG. 6 is a side perspective view of a roller assembly of the holonomic platform.

FIG. 6 shows an embodiment of a roller assembly 120. Each assembly 120 may include a drive ball 124 that is driven by a pair of transmission rollers 126. The assembly 120 may include a retainer ring 128 and a plurality of bushings 130 that captures and allows the ball 124 to rotate in an x and y direction but prevents movement in a z direction. The assembly also holds the ball under the transmission rollers 126.

The transmission rollers 126 are coupled to a motor assembly 132. The assembly 132 corresponds to the motor 88 shown in FIG. 3. The motor assembly 132 includes an output pulley 134 attached to a motor 136. The output pulley 134 is coupled to a pair of ball pulleys 138 by a drive belt 140. The ball pulleys 138 are each attached to a transmission bracket 142. The transmission rollers 126 are attached to the transmission brackets 142.

Rotation of the output pulley 134 rotates the ball pulleys 138. Rotation of the ball pulleys 138 causes the transmission rollers 126 to rotate and spin the ball 124 through frictional forces. Spinning the ball 124 will move the robot 12. The transmission rollers 126 are constructed to always be in contact with the drive ball 124. The brackets 142 allow the transmission rollers 126 to freely spin in a direction orthogonal to the drive direction when one of the other roller assemblies 120 is driving and moving the robot 12.

Figure 7:
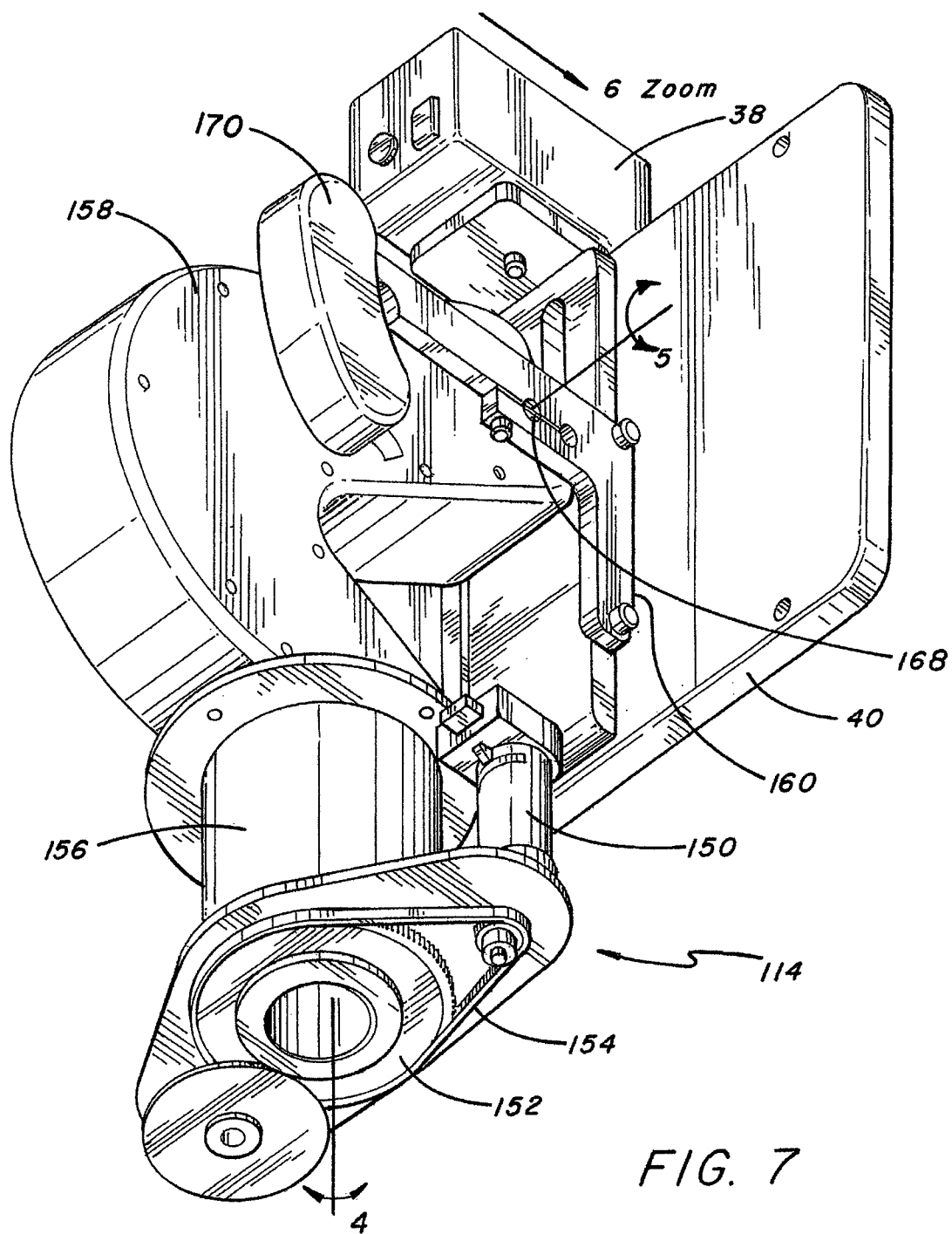
FIG. 7 is a bottom perspective view showing a pedestal assembly of the robot.

As shown in FIG. 7, the pedestal assembly 114 may include a motor 150 that is coupled to a gear 152 by a belt 154. The gear 152 is attached to a shaft 156. The shaft 156 is attached to an arm 158 that is coupled to the camera 38 and monitor 40 by a bracket 160. Activation of the motor 150 rotates the gear 152 and sleeve 156, and causes the camera 38 and monitor 40 to swivel (see also FIG. 4) as indicated by the arrows 4.

Figure 8:
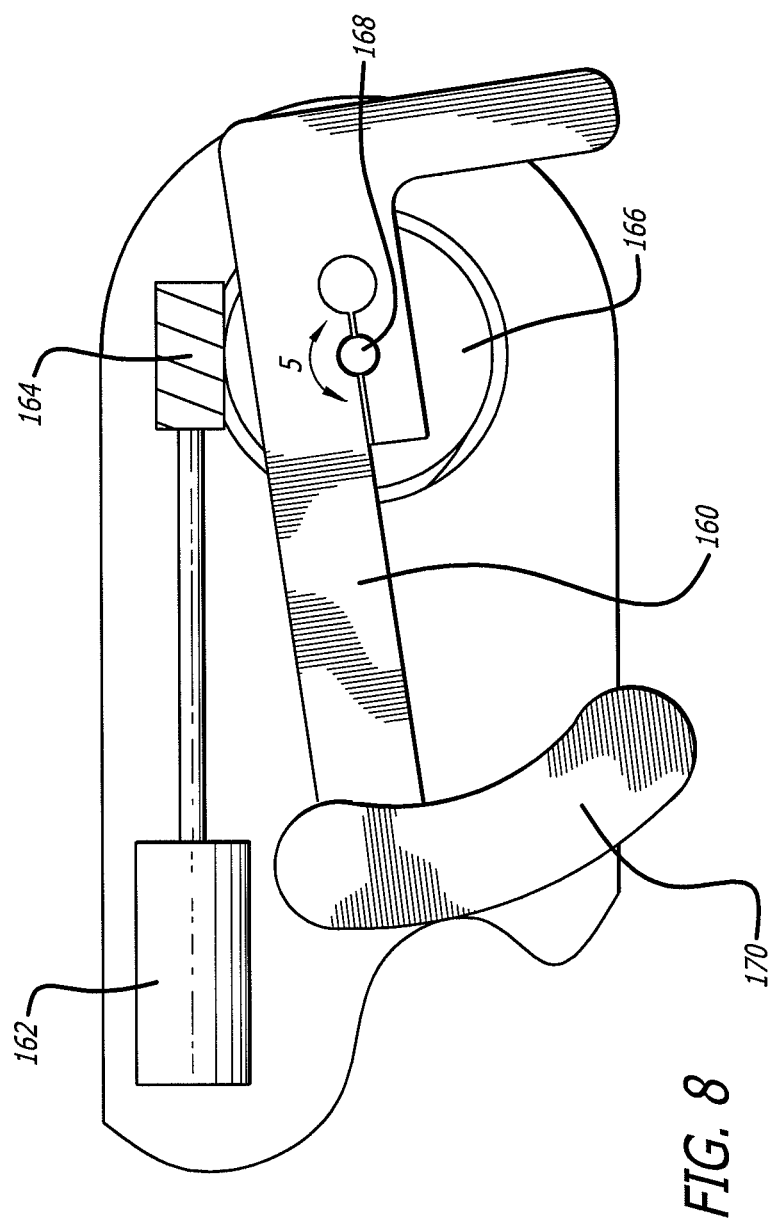
FIG. 8 is a sectional view showing an actuator of the pedestal assembly.

As shown in FIG. 8, the assembly 114 may further include a tilt motor 162 within the arm 158 that can cause the monitor 40 and camera 38 to pivot as indicated by the arrows 5. The tilt motor 162 may rotate a worm 164 that rotates a worm gear 166. The pin 168 is rigidly attached to both the worm gear 166 and the bracket 160 so that rotation of the gear 166 pivots the camera 38 and the monitor 40. The camera 38 may also include a zoom feature to provide yet another degree of freedom for the operator.

In operation, the robot 12 may be placed in a home or a facility where one or more patients are to be monitored and/or assisted. The facility may be a hospital or a residential care facility. By way of example, the robot 12 may be placed in a home where a health care provider may monitor and/or assist the patient. Likewise, a friend or family member may communicate with the patient. The cameras and monitors at both the robot and remote control stations allow for teleconferencing between the patient and the person at the remote station(s).

The robot 12 can be maneuvered through the home or facility by manipulating the input device 32 at a remote station 16. The robot 10 may be controlled by a number of different users. To accommodate for this the robot may have an arbitration system. The arbitration system may be integrated into the operating system of the robot 12. For example, the arbitration technique may be embedded into the operating system of the high-level controller 50.

By way of example, the users may be divided into classes that include the robot itself, a local user, a caregiver, a doctor, a family member, or a service provider. The robot 12 may override input commands that conflict with robot operation. For example, if the robot runs into a wall, the system may ignore all additional commands to continue in the direction of the wall. A local user is a person who is physically present with the robot. The robot could have an input device that allows local operation. For example, the robot may incorporate a voice recognition system that receives and interprets audible commands.

A caregiver is someone who remotely monitors the patient. A doctor is a medical professional who can remotely control the robot and also access medical files contained in the robot memory. The family and service users remotely access the robot. The service user may service the system such as by upgrading software, or setting operational parameters.

The robot 12 may operate in one of two different modes; an exclusive mode, or a sharing mode. In the exclusive mode only one user has access control of the robot. The exclusive mode may have a priority assigned to each type of user. By way of example, the priority may be in order of local, doctor, caregiver, family and then service user. In the sharing mode two or more users may share access with the robot. For example, a caregiver may have access to the robot, the caregiver may then enter the sharing mode to allow a doctor to also access the robot. Both the caregiver and the doctor can conduct a simultaneous tele-conference with the patient.

The arbitration scheme may have one of four mechanisms; notification, timeouts, queue and call back. The notification mechanism may inform either a present user or a requesting user that another user has, or wants, access to the robot. The timeout mechanism gives certain types of users a prescribed amount of time to finish access to the robot. The queue mechanism is an orderly waiting list for access to the robot. The call back mechanism informs a user that the robot can be accessed. By way of example, a family user may receive an e-mail message that the robot is free for usage. Tables I and II, show how the mechanisms resolve access request from the various users.

TABLE I

| User | Access Control | Medical Record | Command Override | Software/Debug Access | Set Priority |
|---|---|---|---|---|---|
| Robot | No | No | Yes (1) | No | No |
| Local | No | No | Yes (2) | No | No |
| Caregiver | Yes | Yes | Yes (3) | No | No |
| Doctor | No | Yes | No | No | No |
| Family | No | No | No | No | No |
| Service | Yes | No | Yes | Yes | Yes |

TABLE II

| | | Requesting User | | | | |
|---|---|---|---|---|---|---|
| | | Local | Caregiver | Doctor | Family | Service |
| Current User | Local | Not Allowed | Warn current user of pending user<br>Notify requesting user that system is in use<br>Set timeout | Warn current user of pending user<br>Notify requesting user that system is in use<br>Set timeout = 5 m | Warn current user of pending user<br>Notify requesting user that system is in use<br>Set timeout = 5 m<br>Call back | Warn current user of pending user<br>Notify requesting user that system is in use<br>No timeout<br>Call back |
| | Caregiver | Warn current user of pending user.<br>Notify requesting user that system is in use.<br>Release control | Not Allowed | Warn current user of pending user<br>Notify requesting user that system is in use<br>Set timeout = 5 m<br>Queue or callback | Warn current user of pending user<br>Notify requesting user that system is in use<br>Set timeout = 5 m | Warn current user of pending user<br>Notify requesting user that system is in use<br>No timeout<br>Callback |
| | Doctor | Warn current user of pending user<br>Notify requesting user that system is in use<br>Release control | Warn current user of pending user<br>Notify requesting user that system is in use<br>Set timeout = 5 m | Warn current user of pending user<br>Notify requesting user that system is in use<br>No timeout<br>Callback | Notify requesting user that system is in use<br>No timeout<br>Queue or callback | Warn current user of pending user<br>Notify requesting user that system is in use<br>No timeout<br>Callback |
| | Family | Warn current user of pending user<br>Notify requesting user that system is in use<br>Release Control | Notify requesting user that system is in use<br>No timeout<br>Put in queue or callback | Warn current user of pending user<br>Notify requesting user that system is in use<br>Set timeout = 1 m | Warn current user of pending user<br>Notify requesting user that system is in use<br>Set timeout = 5 m<br>Queue or callback | Warn current user of pending user<br>Notify requesting user that system is in use<br>No timeout<br>Callback |

TABLE II-continued

| | Requesting User | | | | |
|---|---|---|---|---|---|
| | Local | Caregiver | Doctor | Family | Service |
| Service | Warn current user of pending user Notify requesting user that system is in use No timeout | Notify requesting user that system is in use No timeout Callback | Warn current user of request Notify requesting user that system is in use No timeout Callback | Warn current user of pending user Notify requesting user that system is in use No timeout Queue or callback | Not Allowed |

The information transmitted between the station 16 and the robot 12 may be encrypted. Additionally, the user may have to enter a password to enter the system 10. A selected robot is then given an electronic key by the station 16. The robot 12 validates the key and returns another key to the station 16. The keys are used to encrypt information transmitted in the session.

The robot 12 and remote station 16 transmit commands through the broadband network 18. The commands can be generated by the user in a variety of ways. For example, commands to move the robot may be generated by moving the joystick 32 (see FIG. 1). The commands are preferably assembled into packets in accordance with TCP/IP protocol. Table III provides a list of control commands that are generated at the remote station and transmitted to the robot through the network.

TABLE III

Control Commands

| Command | Example | Description |
|---|---|---|
| drive | drive 10.0 0.0 5.0 | The drive command directs the robot to move at the specified velocity (in cm/sec) in the (x, y) plane, and turn its facing at the specified rate (degrees/sec). |
| goodbye | goodbye | The goodbye command terminates a user session and relinquishes control of the robot |
| gotoHomePosition | gotoHomePosition 1 | The gotoHomePosition command moves the head to a fixed "home" position (pan and tilt), and restores zoom to default value. The index value can be 0, 1, or 2. The exact pan/tilt values for each index are specified in robot configuration files. |
| head | head vel pan 5.0 tilt 10.0 | The head command controls the head motion. It can send commands in two modes, identified by keyword: either positional ("pos") or velocity ("vol"). In velocity mode, the pan and tilt values are desired velocities of the head on the pan and tilt axes, in degree/sec. A single command can include just the pan section, or just the tilt section, or both. |
| keepalive | keepalive | The keepalive command causes no action, but keeps the communication (socket) link open so that a session can continue. In scripts, it can be used to introduce delay time into the action. |
| odometry | odometry 5 | The odometry command enables the flow of odometry messages from the robot. The argument is the number of times odometry is to be reported each second. A value of 0 turns odometry off. |
| reboot | reboot | The reboot command causes the robot computer to reboot immediately. The ongoing session is immediately broken off. |
| restoreHeadPosition | restoreHeadPosition | The restoreHeadPosition functions like the gotoHomePosition command, but it homes the head to a position previously saved with gotoHomePosition. |
| saveHeadPosition | saveHeadPosition | The saveHeadPosition command causes the robot to save the current head position (pan and tilt) in a scratch location in temporary storage so that this position can be restored. Subsequent calls to "restoreHeadPosition" will restore this saved position. Each call to saveHeadPosition overwrites any previously saved position. |

TABLE III-continued

Control Commands

| Command | Example | Description |
| --- | --- | --- |
| setCameraFocus | setCameraFocus 100.0 | The setCameraFocus command controls focus for the camera on the robot side. The value sent is passed "raw" to the video application running on the robot, which interprets it according to its own specification. |
| setCameraZoom | setCameraZoom 100.0 | The setCameraZoom command controls zoom for the camera on the robot side. The value sent is passed "raw" to the video application running on the robot, which interprets it according to its own specification. |
| shutdown | Shutdown | The shutdown command shuts down the robot and powers down its computer. |
| stop | stop | The stop command directs the robot to stop moving immediately. It is assumed this will be as sudden a stop as the mechanism can safely accommodate. |
| timing | Timing 3245629 500 | The timing message is used to estimate message latency. It holds the UCT value (seconds + milliseconds) of the time the message was sent, as recorded on the sending machine. To do a valid test, you must compare results in each direction (i.e., sending from machine A to machine B, then from machine B to machine A) in order to account for differences in the clocks between the two machines. The robot records data internally to estimate average and maximum latency over the course of a session, which it prints to log files. |
| userTask | userTask "Jane Doe" "Remote Visit" | The userTask command notifies the robot of the current user and task. It typically is sent once at the start of the session, although it can be sent during a session if the user and/or task change. The robot uses this information for record-keeping. |

Table IV provides a list of reporting commands that are generated by the robot and transmitted to the remote station through the network.

TABLE IV

Reporting Commands

| Command | Example | Description |
| --- | --- | --- |
| abnormalExit | abnormalExit | This message informs the user that the robot software has crashed or otherwise exited abnormally. Te robot software catches top-level exceptions and generates this message if any such exceptions occur. |
| bodyType | bodyType 3 | The bodyType message informs the station which type body (using the numbering of the mechanical team) the current robot has. This allows the robot to be drawn correctly in the station user interface, and allows for any other necessary body-specific adjustments. |
| driveEnabled | driveEnabled true | This message is sent at the start of a session to indicate whether the drive system is operational. |
| emergencyShutdown | emergencyShutdown | This message informs the station that the robot software has detected a possible "runaway" condition (an failure causing the robot to move out of control) and is shutting the entire system down to prevent hazardous motion. |

TABLE IV-continued

Reporting Commands

| Command | Example | Description |
| --- | --- | --- |
| odometry | odometry 10 20 340 | The odometry command reports the current (x, y) position (cm) and body orientation (degrees) of the robot, in the original coordinate space of the robot at the start of the session. |
| sensorGroup | group_data | Sensors on the robot are arranged into groups, each group of a single type (bumps, range sensors, charge meter, etc.) The sensorGroup message is sent once per group at the start of each session. It contains the number, type, locations, and any other relevant data for the sensors in that group. The station assumes nothing about the equipment carried on the robot; everything it knows about the sensors comes from the sensorGroup messages. |
| sensorState | groupName state data | The sensorState command reports the current state values for a specified group of sensor. The syntax and interpretation for the state data is specific to each group. This message is sent once for each group at each sensor evaluation (normally several times per second). |
| systemError | systemError driveController | This message informs the station user of a failure in one of the robot's subsystems. The error_type argument indicates which subsystem failed, including driveController, sensorController, headHome. |
| systemInfo | systemInfo wireless 45 | This message allows regular reporting of information that falls outside the sensor system such as wireless signal strength. |
| text | text "This is some text" | The text string sends a text string from the robot to the station, where the string is displayed to the user. This message is used mainly for debugging. |
| version | version 1.6 | This message identifies the software version currently running on the robot. It is sent once at the start of the session to allow the station to do any necessary backward compatibility adjustments. |

Figure 9:
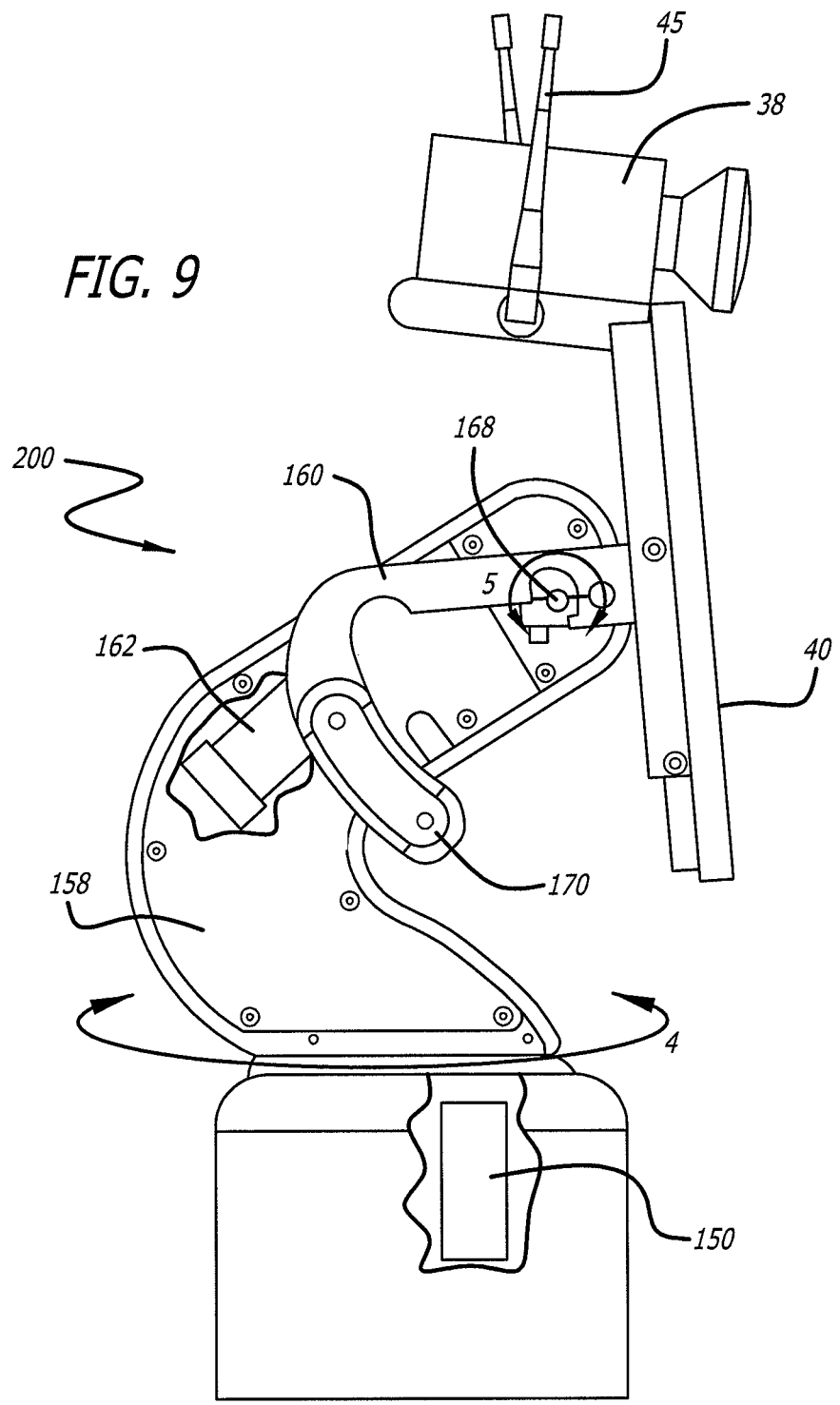
FIG. 9 is a side view of a robot head.

FIG. 9 shows a robot head 200 that can both pivot and spin the camera 38 and the monitor 40. The robot head 200 can be similar to the robot 12 but without the platform 110. The robot head 200 may have the same mechanisms and parts to both pivot the camera 38 and monitor 40 about the pivot axis 4, and spin the camera 38 and monitor 40 about the spin axis 5. The pivot axis may intersect the spin axis. Having a robot head 200 that both pivots and spins provides a wide viewing area. The robot head 200 may be in the system either with or instead of the mobile robot 12.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A robot system that communicates through a broadband network, comprising:
a robot that has a camera and a monitor, said robot generates at least one reporting command that describes a group of sensors on the robot and does not contain sensed data from the sensors, the reporting command is transmitted through the broadband network; and,
a remote station that has a camera and a monitor, said remote station generates at least one control command that is transmitted through the broadband network, and receives the reporting command from said robot.

2. A method for controlling a robot through a broadband network, comprising:
generating at least one control command at a remote station that has a camera and a monitor;
transmitting the control command through a broadband network;
receiving the control command at a robot that has a camera and a monitor;
generating at least one reporting command at the robot, the reporting command describes a group of sensors on the robot and does contain sensed data from the sensors;
transmitting the reporting command through the broadband network; and,
receiving the reporting command at the remote station.

* * * * *